US011324495B2

(12) United States Patent
von Oepen et al.

(10) Patent No.: US 11,324,495 B2
(45) Date of Patent: May 10, 2022

(54) SYSTEMS AND METHODS FOR DELIVERING AN INTRAVASCULAR DEVICE TO THE MITRAL ANNULUS

(71) Applicant: Cephea Valve Technologies, Inc., Santa Clara, CA (US)

(72) Inventors: Randolf von Oepen, Aptos, CA (US); Sean A. McNiven, Menlo Park, CA (US); Francisco Valencia, East Palo Alto, CA (US)

(73) Assignee: CEPHEA VALVE TECHNOLOGIES, INC., Santa Clara, CA (US)

( * ) Notice: Subject to any disclaimer, the term of this patent is extended or adjusted under 35 U.S.C. 154(b) by 0 days.

(21) Appl. No.: 15/662,142

(22) Filed: Jul. 27, 2017

(65) Prior Publication Data

US 2018/0028177 A1 Feb. 1, 2018

Related U.S. Application Data

(60) Provisional application No. 62/462,776, filed on Feb. 23, 2017, provisional application No. 62/436,926, (Continued)

(51) Int. Cl.
*A61F 2/24* (2006.01)
*A61B 17/04* (2006.01)
(Continued)

(52) U.S. Cl.
CPC ........ *A61B 17/0469* (2013.01); *A61F 2/2436* (2013.01); *A61F 2/2439* (2013.01);
(Continued)

(58) Field of Classification Search
CPC .... A61F 2/2466; A61F 2/2436; A61F 2/2427; A61M 25/0147; A61M 25/0105;
(Continued)

(56) References Cited

U.S. PATENT DOCUMENTS 4,406,656 A 9/1983 Hattler et al.
4,728,319 A 3/1988 Masch
(Continued)

FOREIGN PATENT DOCUMENTS

CN 1469724 1/2004
CN 1688352 A 10/2005
(Continued)

OTHER PUBLICATIONS

U.S. Appl. No. 15/661,988, filed Jul. 27, 2017, von Oepen et al.
(Continued)

*Primary Examiner* — Diane D Yabut
*Assistant Examiner* — Christina C Lauer
(74) *Attorney, Agent, or Firm* — Workman Nydegger

(57) ABSTRACT

The present disclosure describes devices, systems, and methods for intravascularly delivering an implantable device at the mitral annulus. A delivery system includes a delivery member coupled to a handle assembly and extending distally from the handle assembly. The intravascular device is attached at the distal end of the delivery member, and is housed within a distal piece of an outer sheath. A steering catheter is nested within the outer sheath to bend the delivery member into position. A delivery catheter is configured to advance the intravascular device relative to the outer sheath, and a suture catheter includes sutures/tethers which may be coupled to the intravascular device prior to deployment.

19 Claims, 19 Drawing Sheets

Related U.S. Application Data filed on Dec. 20, 2016, provisional application No. 62/436,985, filed on Dec. 20, 2016, provisional application No. 62/436,913, filed on Dec. 20, 2016, provisional application No. 62/436,918, filed on Dec. 20, 2016, provisional application No. 62/436,922, filed on Dec. 20, 2016, provisional application No. 62/436,887, filed on Dec. 20, 2016, provisional application No. 62/430,149, filed on Dec. 5, 2016, provisional application No. 62/430,143, filed on Dec. 5, 2016, provisional application No. 62/422,426, filed on Nov. 15, 2016, provisional application No. 62/404,511, filed on Oct. 5, 2016, provisional application No. 62/380,888, filed on Aug. 29, 2016, provisional application No. 62/380,873, filed on Aug. 29, 2016, provisional application No. 62/380,862, filed on Aug. 29, 2016, provisional application No. 62/380,795, filed on Aug. 29, 2016, provisional application No. 62/380,799, filed on Aug. 29, 2016, provisional application No. 62/380,246, filed on Aug. 26, 2016, provisional application No. 62/368,702, filed on Jul. 29, 2016, provisional application No. 62/368,695, filed on Jul. 29, 2016, provisional application No. 62/368,711, filed on Jul. 29, 2016, provisional application No. 62/368,683, filed on Jul. 29, 2016.

(51) Int. Cl.
  *A61M 25/01* (2006.01)
  *A61M 25/00* (2006.01)
  *A61M 25/09* (2006.01)
  *A61F 2/95* (2013.01)
  *A61M 25/06* (2006.01)

(52) U.S. Cl.
  CPC ...... *A61M 25/005* (2013.01); *A61M 25/0045* (2013.01); *A61M 25/0054* (2013.01); *A61M 25/0136* (2013.01); *A61M 25/0138* (2013.01); *A61M 25/0147* (2013.01); *A61M 25/09* (2013.01); *A61F 2/9517* (2020.05); *A61M 25/0097* (2013.01); *A61M 25/0662* (2013.01); *A61M 2025/0004* (2013.01); *A61M 2025/0175* (2013.01)

(58) Field of Classification Search
  CPC .......... A61M 25/0138; A61M 25/0054; A61M 25/09; A61M 25/0136; A61M 25/0133; A61B 17/0469
  See application file for complete search history.

(56) References Cited

U.S. PATENT DOCUMENTS

| | | | |
|---|---|---|---|
| 5,053,043 A * | 10/1991 | Gottesman | A61B 17/0482 128/898 |
| 5,059,213 A | 10/1991 | Chesterfield et al. | |
| 5,078,722 A | 1/1992 | Stevens | |
| 5,078,723 A | 1/1992 | Dance et al. | |
| 5,236,450 A | 8/1993 | Scott | |
| 5,325,845 A | 7/1994 | Adair | |
| 5,345,945 A | 9/1994 | Hodgson et al. | |
| 5,387,219 A | 2/1995 | Rappe | |
| 5,415,664 A | 5/1995 | Pinchuk | |
| 5,472,423 A | 12/1995 | Gronauer | |
| 5,571,085 A | 11/1996 | Accisano, III | |
| 5,662,606 A | 9/1997 | Cimino et al. | |
| 5,669,919 A | 9/1997 | Sanders et al. | |
| 5,769,812 A | 6/1998 | Stevens et al. | |
| 5,807,405 A | 9/1998 | Vanney et al. | |
| 5,820,591 A * | 10/1998 | Thompson | A61M 25/0136 604/95.01 |
| 5,843,103 A | 12/1998 | Wulfman | |
| 5,855,601 A | 1/1999 | Bessler et al. | |
| 5,873,882 A * | 2/1999 | Straub | A61B 17/320783 606/159 |
| 5,902,334 A | 5/1999 | Dwyer et al. | |
| 5,906,642 A | 5/1999 | Caudillo et al. | |
| 5,957,973 A | 9/1999 | Quiachon et al. | |
| 6,090,118 A | 7/2000 | McGuckin, Jr. | |
| 6,180,059 B1 | 1/2001 | Divino, Jr et al. | |
| 6,228,110 B1 | 5/2001 | Munsinger | |
| 6,458,137 B1 | 10/2002 | Klint | |
| 6,517,550 B1 | 2/2003 | Konya et al. | |
| 6,695,836 B1 * | 2/2004 | DeMello | A61B 18/1492 606/27 |
| 6,926,725 B2 | 8/2005 | Cooke et al. | |
| 7,172,617 B2 | 2/2007 | Colgan et al. | |
| 7,344,553 B2 | 3/2008 | Opolski et al. | |
| 7,666,204 B2 | 2/2010 | Thornton et al. | |
| 7,736,388 B2 | 6/2010 | Goldfarb et al. | |
| 7,837,727 B2 | 11/2010 | Goetz et al. | |
| 7,988,724 B2 | 8/2011 | Salahieh et al. | |
| 7,993,303 B2 | 8/2011 | Von Oepen et al. | |
| 8,157,852 B2 | 4/2012 | Bloom et al. | |
| 8,523,881 B2 | 9/2013 | Cabiri et al. | |
| 8,647,323 B2 | 2/2014 | Guo et al. | |
| 8,911,455 B2 | 12/2014 | Quadri et al. | |
| 8,926,588 B2 | 1/2015 | Berthiaume et al. | |
| 8,926,692 B2 | 1/2015 | Dwork | |
| 9,339,378 B2 | 5/2016 | Quadri et al. | |
| 9,370,423 B2 | 6/2016 | Ryan | |
| 9,393,112 B2 | 7/2016 | Tuval et al. | |
| 9,399,112 B2 | 7/2016 | Shevgoor et al. | |
| 9,668,859 B2 | 6/2017 | Kheradvar et al. | |
| 9,687,373 B2 | 6/2017 | Vad | |
| 9,693,862 B2 | 7/2017 | Campbell et al. | |
| 9,801,745 B2 | 10/2017 | Wubbeling et al. | |
| 10,111,671 B2 | 10/2018 | Bodewadt | |
| 10,117,760 B2 | 11/2018 | Mangiardi | |
| 10,376,673 B2 | 8/2019 | Van Hoven et al. | |
| 10,398,553 B2 | 9/2019 | Kizuka | |
| 10,470,902 B2 | 11/2019 | Sheldon et al. | |
| 2001/0002445 A1 | 5/2001 | Vesely | |
| 2001/0047150 A1 | 11/2001 | Chobotov | |
| 2002/0013547 A1 | 1/2002 | Paskar | |
| 2004/0049207 A1 | 3/2004 | Goldfarb et al. | |
| 2004/0064179 A1 * | 4/2004 | Linder | A61F 2/013 623/1.11 |
| 2004/0116848 A1 | 6/2004 | Gardeski et al. | |
| 2004/0127849 A1 | 7/2004 | Kantor | |
| 2004/0133232 A1 | 7/2004 | Rosenbluth et al. | |
| 2004/0147826 A1 | 7/2004 | Peterson | |
| 2005/0038383 A1 | 2/2005 | Kelley et al. | |
| 2005/0085903 A1 | 4/2005 | Lau | |
| 2005/0137695 A1 | 6/2005 | Salahieh et al. | |
| 2005/0143809 A1 | 6/2005 | Salahieh et al. | |
| 2005/0256452 A1 | 11/2005 | DeMarchi et al. | |
| 2005/0259452 A1 | 11/2005 | DeMarchi et al. | |
| 2005/0283231 A1 | 11/2005 | Haug et al. | |
| 2005/0277874 A1 | 12/2005 | Selkee | |
| 2005/0277876 A1 | 12/2005 | Hayden | |
| 2005/0288768 A1 | 12/2005 | Sowinski et al. | |
| 2006/0135961 A1 * | 6/2006 | Rosenman | A61M 25/0045 606/108 |
| 2007/0060997 A1 | 3/2007 | de Boer | |
| 2007/0118155 A1 | 5/2007 | Goldfarb et al. | |
| 2007/0156225 A1 | 7/2007 | George et al. | |
| 2007/0173757 A1 | 7/2007 | Levine et al. | |
| 2007/0197858 A1 | 8/2007 | Goldfarb et al. | |
| 2007/0203561 A1 | 8/2007 | Forster et al. | |
| 2007/0260225 A1 | 11/2007 | Sakakine et al. | |
| 2007/0270779 A1 | 11/2007 | Jacobs et al. | |
| 2007/0299424 A1 | 12/2007 | Cumming et al. | |
| 2008/0058722 A1 | 3/2008 | Von Oepen et al. | |
| 2008/0103585 A1 | 5/2008 | Monstadt et al. | |
| 2008/0109065 A1 | 5/2008 | Bowe | |
| 2008/0188850 A1 | 8/2008 | Mody et al. | |
| 2008/0195126 A1 | 8/2008 | Solem | |

(56) References Cited

U.S. PATENT DOCUMENTS

| | | |
|---|---|---|
| 2009/0036768 A1 | 2/2009 | Seehusen et al. |
| 2009/0069885 A1 | 3/2009 | Rahdert et al. |
| 2009/0099554 A1 | 4/2009 | Forster et al. |
| 2009/0163934 A1 | 6/2009 | Raschdorf, Jr. et al. |
| 2009/0182407 A1 | 7/2009 | Leanna et al. |
| 2009/0204005 A1* | 8/2009 | Keast .................. A61B 1/018 600/461 |
| 2009/0240326 A1 | 9/2009 | Wilson et al. |
| 2009/0276039 A1 | 11/2009 | Meretei |
| 2009/0281619 A1 | 11/2009 | Le et al. |
| 2010/0004739 A1 | 1/2010 | Vesely |
| 2010/0044410 A1 | 2/2010 | Argentine et al. |
| 2010/0059173 A1 | 3/2010 | Kampa et al. |
| 2010/0070009 A1 | 3/2010 | Barker |
| 2010/0217261 A1 | 8/2010 | Watson |
| 2010/0249894 A1 | 9/2010 | Oba et al. |
| 2010/0331776 A1* | 12/2010 | Salahieh .......... A61M 25/0136 604/95.04 |
| 2011/0112630 A1 | 5/2011 | Groothuis et al. |
| 2011/0166566 A1 | 7/2011 | Gabriel |
| 2011/0166649 A1 | 7/2011 | Gross et al. |
| 2011/0202128 A1 | 8/2011 | Duffy |
| 2011/0257718 A1 | 10/2011 | Argentine |
| 2011/0307049 A1 | 12/2011 | Kao |
| 2011/0319904 A1 | 12/2011 | Hollett et al. |
| 2012/0022640 A1 | 1/2012 | Gross et al. |
| 2012/0065464 A1 | 3/2012 | Elllis et al. |
| 2012/0109078 A1 | 5/2012 | Schaeffer |
| 2012/0172915 A1 | 7/2012 | Fifer et al. |
| 2012/0316639 A1 | 12/2012 | Kleinschrodt |
| 2012/0330348 A1 | 12/2012 | Strauss et al. |
| 2012/0330408 A1 | 12/2012 | Hillukka et al. |
| 2013/0030514 A1 | 1/2013 | Kasprzak et al. |
| 2013/0041314 A1 | 2/2013 | Dillon |
| 2013/0066342 A1 | 3/2013 | Dell et al. |
| 2013/0103001 A1 | 4/2013 | BenMaamer et al. |
| 2013/0109910 A1 | 5/2013 | Alexander et al. |
| 2013/0131775 A1 | 5/2013 | Hadley et al. |
| 2013/0289696 A1 | 10/2013 | Maggard et al. |
| 2014/0107693 A1 | 4/2014 | Plassman |
| 2014/0114390 A1* | 4/2014 | Tobis ................ A61B 17/0401 623/1.11 |
| 2014/0142688 A1 | 5/2014 | Duffy et al. |
| 2014/0148889 A1 | 5/2014 | Deshmukh et al. |
| 2014/0180124 A1 | 6/2014 | Whiseant et al. |
| 2014/0200649 A1 | 7/2014 | Essinger et al. |
| 2014/0228871 A1 | 8/2014 | Cohen et al. |
| 2014/0276966 A1 | 9/2014 | Ranucci et al. |
| 2014/0324164 A1 | 10/2014 | Gross et al. |
| 2014/0336744 A1 | 11/2014 | Tani et al. |
| 2014/0379074 A1 | 12/2014 | Spence et al. |
| 2015/0005704 A1 | 1/2015 | Heisel et al. |
| 2015/0005801 A1 | 1/2015 | Marquis et al. |
| 2015/0073341 A1 | 3/2015 | Salahieh et al. |
| 2015/0088189 A1 | 3/2015 | Paul, Jr. |
| 2015/0094656 A1 | 4/2015 | Salahieh et al. |
| 2015/0112430 A1* | 4/2015 | Creaven ................ A61F 2/2436 623/2.11 |
| 2015/0272759 A1 | 10/2015 | Argentine |
| 2015/0306806 A1 | 10/2015 | Dando et al. |
| 2016/0045311 A1 | 2/2016 | McCann et al. |
| 2016/0074163 A1 | 3/2016 | Yang et al. |
| 2016/0113765 A1 | 4/2016 | Ganesan et al. |
| 2016/0143661 A1 | 5/2016 | Wood et al. |
| 2017/0035566 A1 | 2/2017 | Krone et al. |
| 2017/0042678 A1* | 2/2017 | Ganesan .............. A61F 2/2436 |
| 2017/0080186 A1 | 3/2017 | Salahieh et al. |
| 2017/0232238 A1 | 8/2017 | Biller et al. |
| 2018/0028177 A1 | 2/2018 | von Oepen et al. |
| 2018/0028215 A1 | 2/2018 | Cohen |
| 2018/0028305 A1 | 2/2018 | von Oepen et al. |
| 2018/0028779 A1 | 2/2018 | von Oepen et al. |
| 2018/0028787 A1 | 2/2018 | McNiven et al. |
| 2018/0055636 A1 | 3/2018 | Valencia et al. |
| 2018/0055637 A1 | 3/2018 | von Oepen et al. |
| 2018/0056033 A1 | 3/2018 | von Oepen et al. |
| 2018/0056043 A1 | 3/2018 | von Oepen et al. |
| 2018/0071098 A1 | 3/2018 | Alon |
| 2018/0092744 A1 | 4/2018 | von Oepen et al. |
| 2018/0126119 A1 | 5/2018 | McNiven et al. |
| 2018/0132837 A1 | 5/2018 | Mathena et al. |
| 2018/0133454 A1 | 5/2018 | von Oepen et al. |
| 2018/0360457 A1 | 12/2018 | Ellis et al. |
| 2019/0030285 A1 | 1/2019 | Prabhu et al. |
| 2019/0274831 A1 | 9/2019 | Prabhu |
| 2020/0155804 A1 | 5/2020 | von Oepen et al. |
| 2020/0230352 A1 | 7/2020 | Mcniven et al. |
| 2020/0230354 A1 | 7/2020 | Von Oepen et al. |

FOREIGN PATENT DOCUMENTS

| | | |
|---|---|---|
| CN | 1961983 A | 5/2007 |
| CN | 101247847 A | 8/2008 |
| CN | 101426452 A | 5/2009 |
| CN | 101479006 A | 7/2009 |
| CN | 101506538 A | 8/2009 |
| CN | 102159277 A | 8/2011 |
| CN | 102258402 A | 11/2011 |
| CN | 102405022 A | 4/2012 |
| CN | 102481433 A | 5/2012 |
| CN | 102548505 A | 7/2012 |
| CN | 102770080 | 11/2012 |
| CN | 102933161 A | 2/2013 |
| CN | 103517689 A | 1/2014 |
| CN | 103702635 A | 4/2014 |
| CN | 103841899 | 6/2014 |
| CN | 103957993 A | 7/2014 |
| CN | 104203329 A | 12/2014 |
| CN | 104812439 A | 7/2015 |
| CN | 105246434 A | 1/2016 |
| CN | 105899167 A | 8/2016 |
| EP | 1980288 | 4/2008 |
| EP | 1980288 | 10/2008 |
| EP | 2537487 | 12/2012 |
| EP | 2702965 | 3/2014 |
| EP | 3009103 | 4/2016 |
| GN | 1859942 A | 11/2006 |
| JP | 06-343702 A | 12/1994 |
| JP | 2003062072 | 3/2003 |
| JP | 2006528911 | 12/2006 |
| JP | 2013516244 | 5/2013 |
| WO | 98/57698 A1 | 12/1998 |
| WO | WO 2001051114 | 7/2001 |
| WO | WO 2007044285 | 4/2007 |
| WO | WO 2007136829 | 11/2007 |
| WO | WO 2008103722 | 8/2008 |
| WO | WO 2010024801 | 3/2010 |
| WO | WO 2010121076 | 10/2010 |
| WO | 2011/033783 A1 | 3/2011 |
| WO | WO 2012020521 | 2/2012 |
| WO | 2012/057983 A1 | 5/2012 |
| WO | WO 2012151396 | 11/2012 |
| WO | 2013/126529 A2 | 8/2013 |
| WO | WO 2014064694 | 5/2014 |
| WO | WO 2014121280 | 8/2014 |
| WO | WO 2014128705 | 8/2014 |
| WO | WO 2015191938 | 12/2015 |
| WO | WO 2016022797 | 2/2016 |
| WO | WO 2016112085 | 7/2016 |
| WO | WO 2016144708 | 9/2016 |
| WO | WO 2016150806 | 9/2016 |
| WO | WO 2016183526 | 11/2016 |
| WO | 2017/023534 A2 | 2/2017 |
| WO | WO 2018023038 | 2/2018 |
| WO | WO 2018023043 | 2/2018 |
| WO | WO 2018023044 | 2/2018 |
| WO | WO 2018023045 | 2/2018 |
| WO | WO 2018023052 | 2/2018 |
| WO | WO 2018044446 | 3/2018 |
| WO | WO 2018044447 | 3/2018 |
| WO | WO 2018044448 | 3/2018 |
| WO | WO 2018044449 | 3/2018 |

(56) References Cited

FOREIGN PATENT DOCUMENTS

| WO | WO 2018067788 | 4/2018 |
|---|---|---|
| WO | WO 2018093426 | 5/2018 |

OTHER PUBLICATIONS

U.S. Appl. No. 15/662,001, filed Jul. 27, 2017, von Oepen et al.
U.S. Appl. No. 15/662,008, filed Jul. 27, 2017, McNiven et al.
U.S. Appl. No. 15/662,013, filed Jul. 27, 2017, McNiven et al.
U.S. Appl. No. 15/662,014, filed Jul. 27, 2017, von Oepen et al.
U.S. Appl. No. 15/662,066, filed Jul. 27, 2017, von Oepen et al.
U.S. Appl. No. 15/662,076, filed Jul. 27, 2017, von Oepen et al.
U.S. Appl. No. 15/662,089, filed Jul. 27, 2017, von Oepen et al.
U.S. Appl. No. 15/662,093, filed Jul. 27, 2017, von Oepen et al.
U.S. Appl. No. 15/662,098, filed Jul. 27, 2017, Valencia et al.
Takizawa H et al.: "Development of a microfine active bending catheter equipped with MIF tactile sensors", Micro Electro Mechanical Systems, 1999. MEMS '99. Twelfth IEEE International Conference on Orlando, FL, USA Jan. 17-21, 1999, Piscataway, NJ, USA,IEEE, US, Jan. 17, 1999 (Jan. 17, 1999), pp. 412-417, XP010321677, ISBN: 978-0-7803-5194-3 figures 1-3.
U.S. Appl. No. 15/662,001, Jun. 20, 2019, Office Action.
U.S. Appl. No. 15/662,001, Oct. 4, 2019, Office Action.
U.S. Appl. No. 15/662,001, Dec. 18, 2019, Notice of Allowance.
U.S. Appl. No. 15/662,013, Dec. 5, 2019, Advisory Action.
U.S. Appl. No. 15/662,066, Jul. 11, 2019, Office Action.
U.S. Appl. No. 15/662,066, Dec. 16, 2019, Office Action.
U.S. Appl. No. 15/662,076, Oct. 8, 2019, Notice of Allowance.
U.S. Appl. No. 15/662,089, Oct. 7, 2019, Office Action.
U.S. Appl. No. 15/662,093, Mar. 7, 2019, Office Action.
U.S. Appl. No. 15/662,093, Aug. 29, 2019, Office Action.
U.S. Appl. No. 15/662,093, Dec. 3, 2019, Office Action.
U.S. Appl. No. 15/662,008, Sep. 13, 2019, Office Action.
U.S. Appl. No. 15/662,014, May 31, 2019, Office Action.
U.S. Appl. No. 15/662,014, Oct. 2, 2019, Notice of Allowance.
U.S. Appl. No. 15/662,098, Jul. 5, 2019, Office Action.
U.S. Appl. No. 15/724,499, Jul. 15, 2019, Notice of Allowance.
U.S. Appl. No. 15/724,499, Aug. 27, 2019, Notice of Allowance.
U.S. Appl. No. 15/724,499, Nov. 22, 2019, Notice of Allowance.
Hironobu Takizawa et al. "Development of a Microfine Active Bending Catheter Equipped with MIF Tactile Sensors", Micro Electro Mechanical Systems, IEEE, Jan. 17, 1999, pp. 412-417.
U.S. Appl. No. 15/662,013, filed May 7, 2020, Notice of Allowance.
U.S. Appl. No. 15/662,093, filed May 6, 2020, Office Action.
U.S. Appl. No. 15/662,098, filed Apr. 30, 2020, Office Action.
Advisory Action received for U.S. Appl. No. 15/662,093, dated Jul. 9, 2020.
Notice of Allowance received for U.S. Appl. No. 15/724,499, dated Jul. 1, 2020.
Office Action received for U.S. Appl. No. 15/662,008, dated Sep. 13, 2019.
U.S. Appl. No. 15/662,066, filed May 21, 2020, Office Action.
U.S. Appl. No. 15/662,089, filed Jun. 11, 2020, Office Action.
U.S. Appl. No. 15/662,001, filed Mar. 24, 2020, Notice of Allowance.
U.S. Appl. No. 15/662,098, filed Mar. 23, 2020, Advisory Action.
U.S. Appl. No. 15/724,499, filed Mar. 25, 2020, Office Action.
U.S. Appl. No. 15/662,013, Jun. 13, 2019, Office Action.
U.S. Appl. No. 15/662,013, Oct. 10, 2019, Office Action.
U.S. Appl. No. 15/662,066, Feb. 27, 2020, Advisory Action.
U.S. Appl. No. 15/662,076, Jan. 31, 2020, Notice of Allowance.
U.S. Appl. No. 15/662,089, Jan. 10, 2020, Office Action.
U.S. Appl. No. 15/662,008, Jan. 31, 2020, Notice of Allowance.
U.S. Appl. No. 15/662,098, Jan. 27, 2020, Office Action.

* cited by examiner

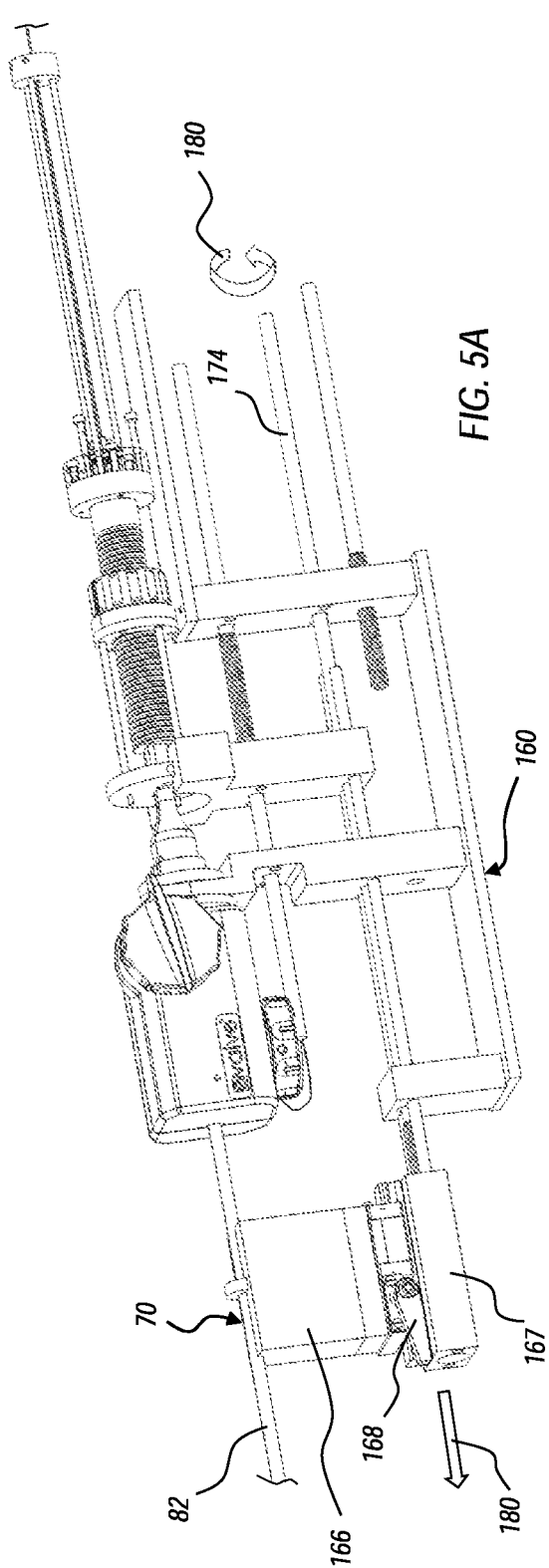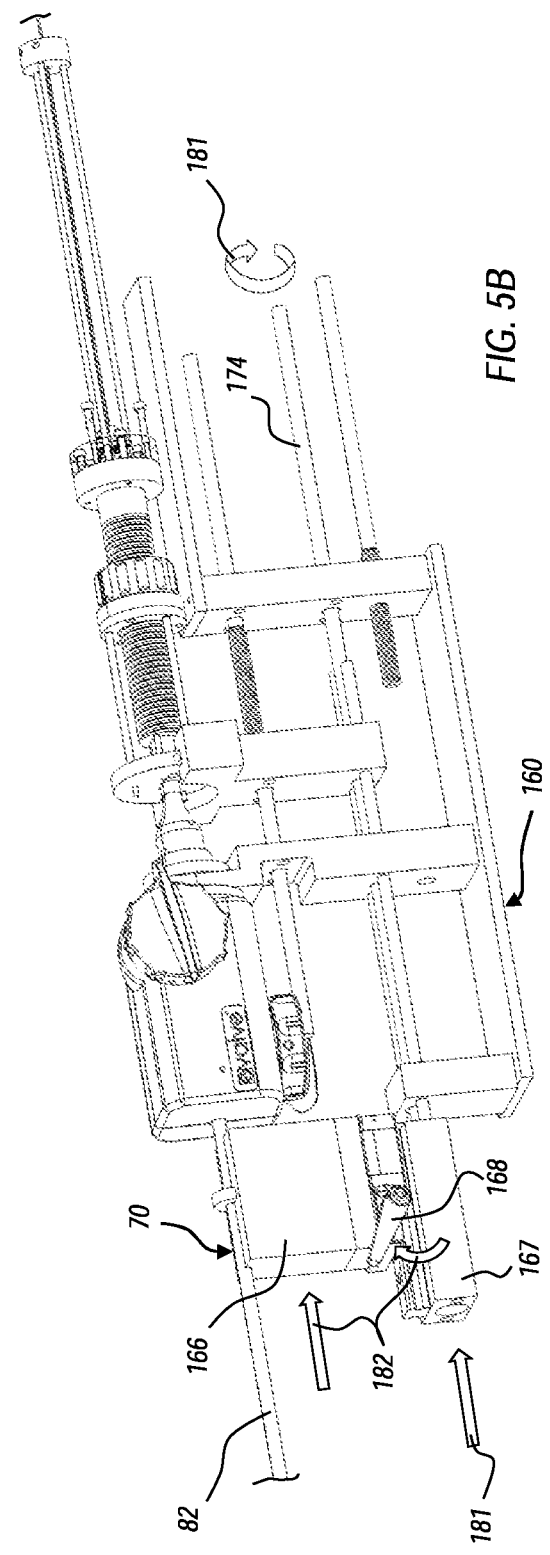
FIG. 5A
FIG. 5B

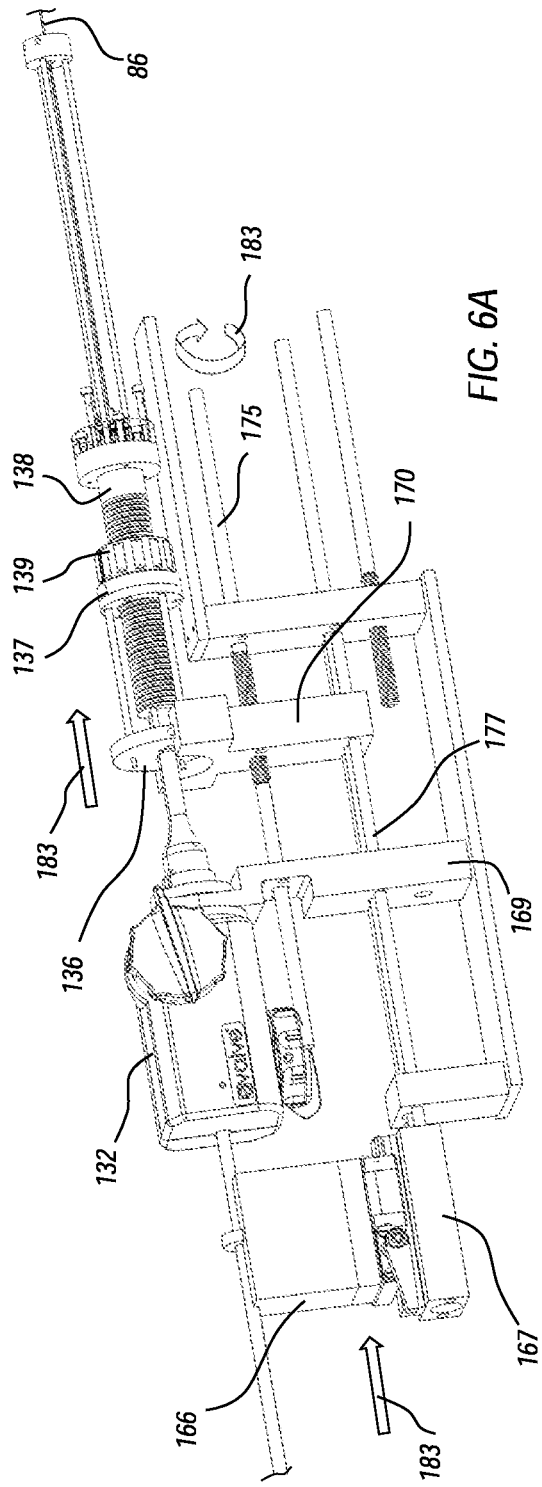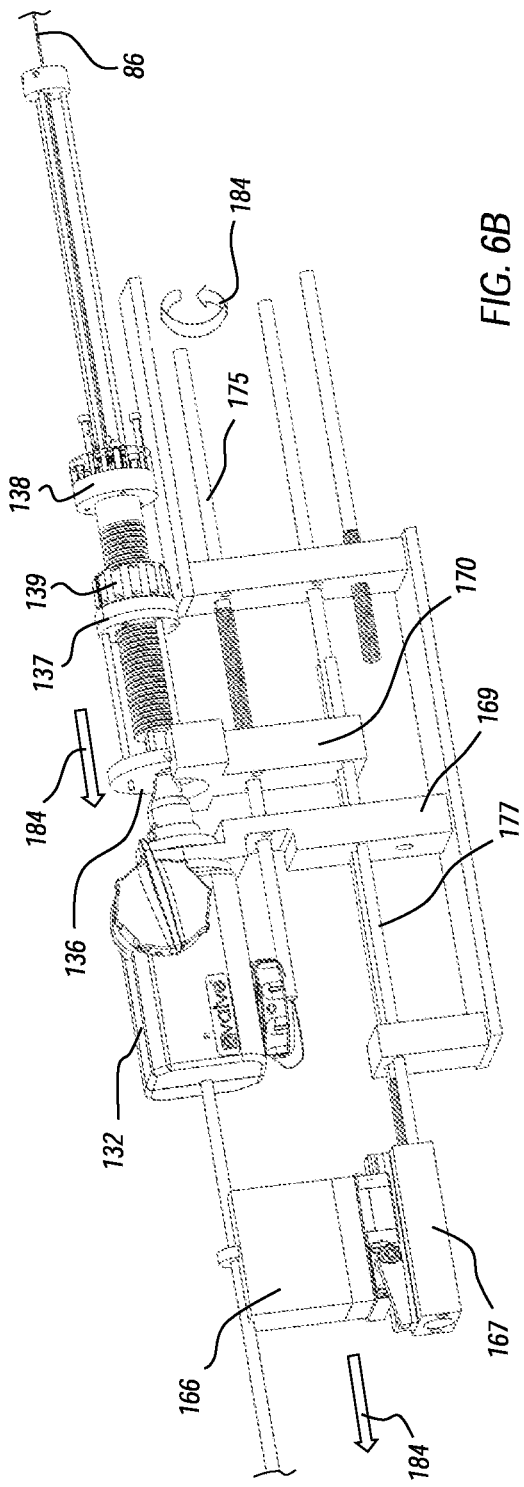
FIG. 6A
FIG. 6B

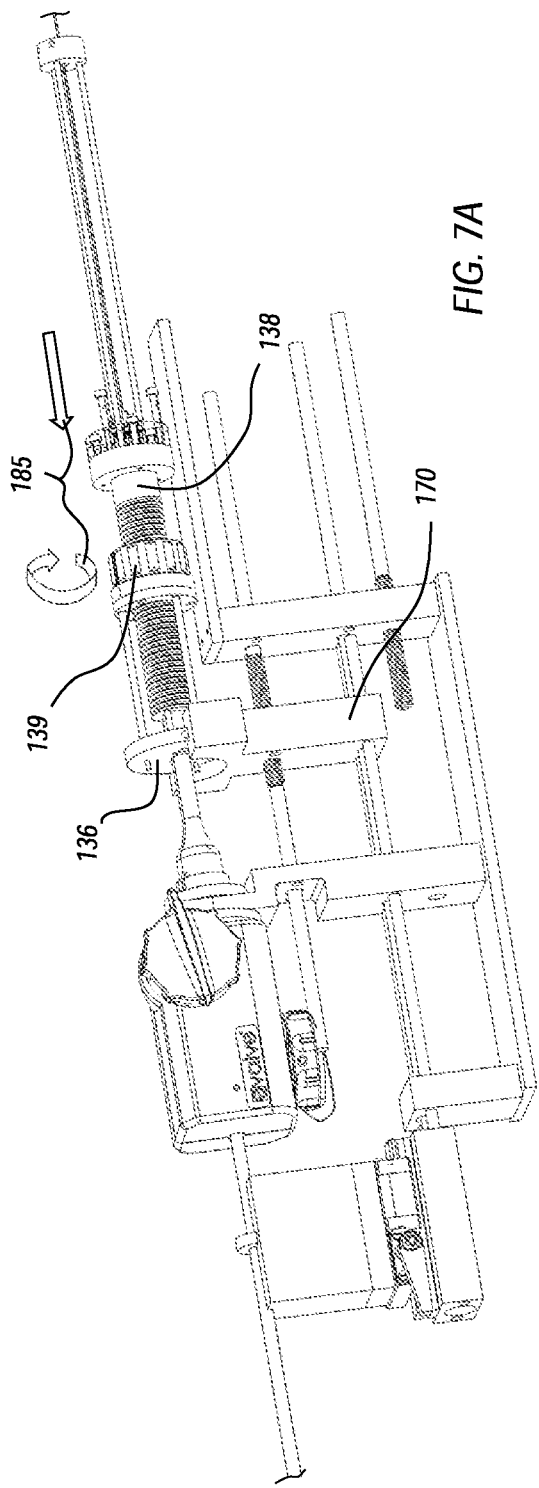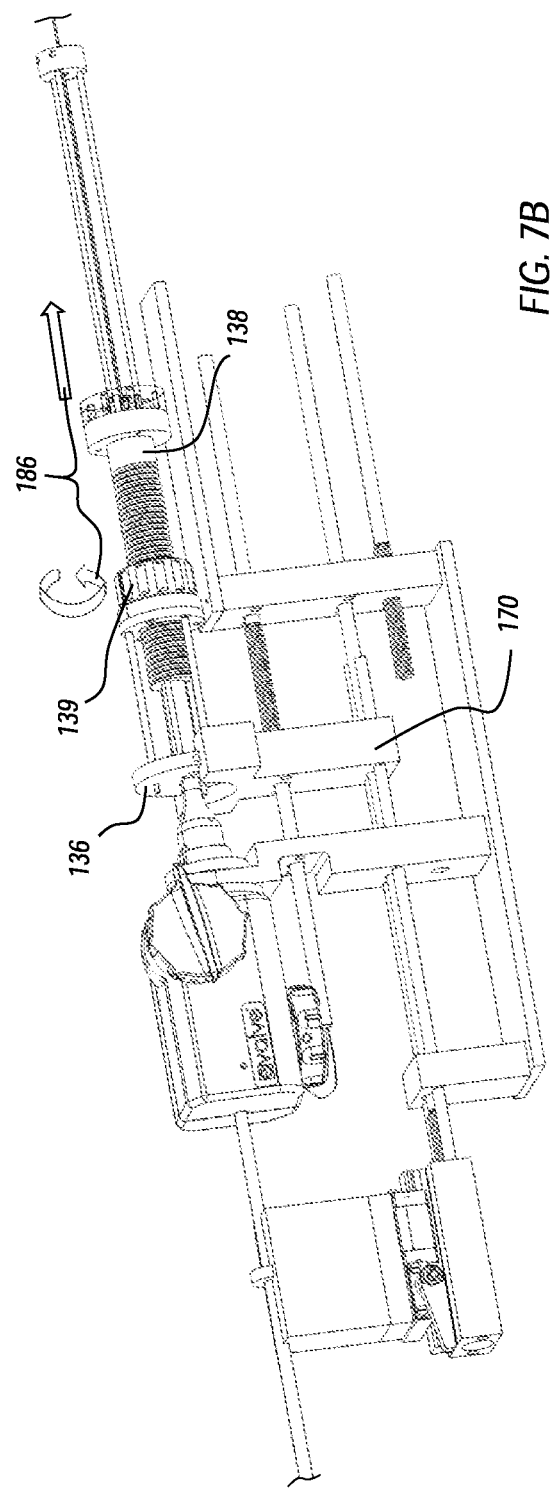
FIG. 7A
FIG. 7B

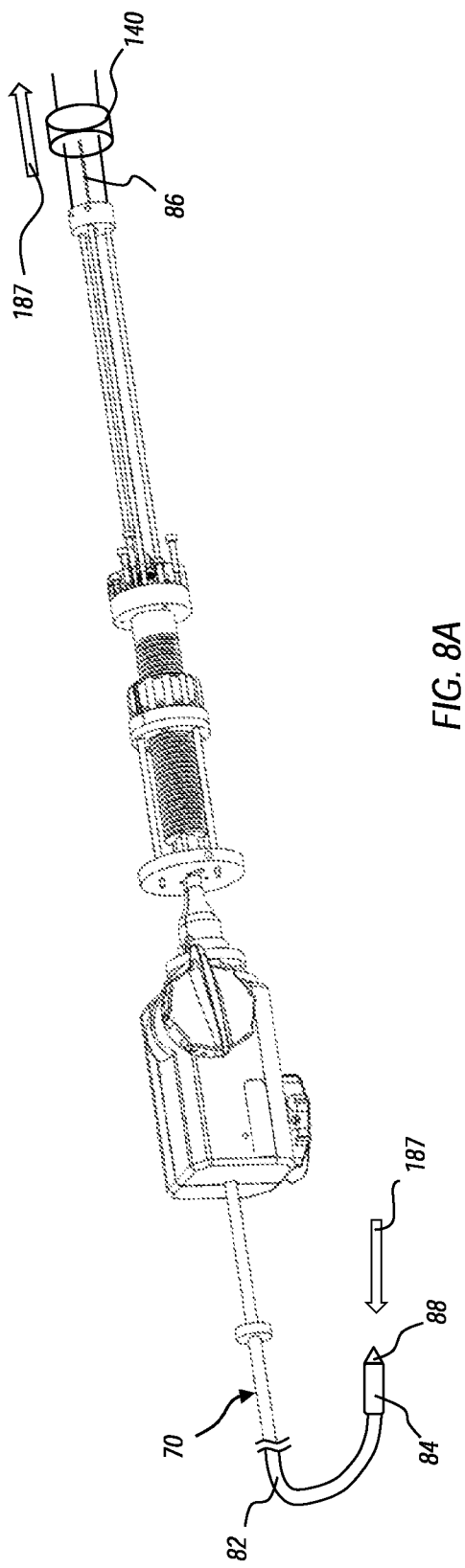
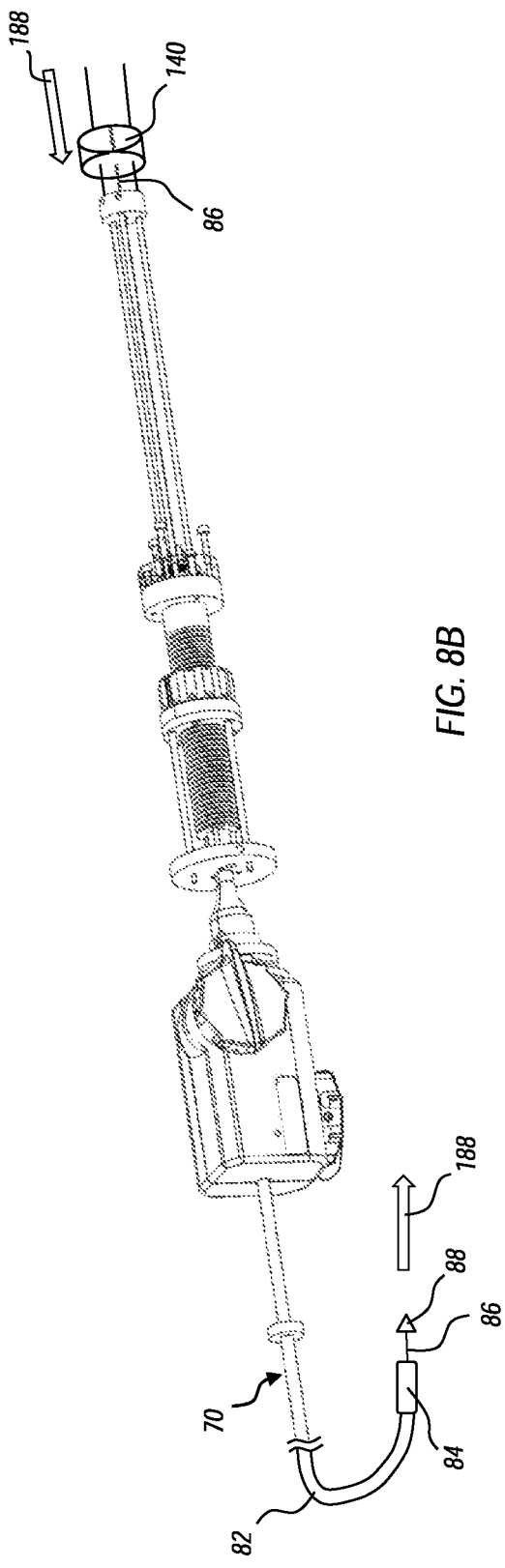
FIG. 8A
FIG. 8B

SYSTEMS AND METHODS FOR DELIVERING AN INTRAVASCULAR DEVICE TO THE MITRAL ANNULUS

CROSS-REFERENCE TO RELATED APPLICATIONS

This application claims the benefit of and priority to: U.S. Provisional Patent Application Ser. No. 62/368,683, filed on Jul. 29, 2016 and titled "Intravascular Device Delivery Sheath"; U.S. Provisional Patent Application Ser. No. 62/368,695, filed on Jul. 29, 2016 and titled "Threaded Coil"; U.S. Provisional Patent Application Ser. No. 62/368,702, filed on Jul. 29, 2016 and titled "Combination Steerable Catheter and Systems"; U.S. Provisional Patent Application Ser. No. 62/368,711, filed on Jul. 29, 2016, and titled "Hypotube Reinforced Intravascular Device Delivery Systems and Methods"; U.S. Provisional Patent Application Ser. No. 62/380,246, filed on Aug. 26, 2016 and titled "Rotational Fixation of Catheters"; U.S. Provisional Patent Application Ser. No. 62/380,795, filed Aug. 29, 2016 and titled "Systems and Methods for Loading and Deploying an Intravascular Device"; U.S. Provisional Patent Application Ser. No. 62/380,799, filed Aug. 29, 2016 and titled "Moveable Guidewire Lumen"; U.S. Provisional Patent Application Ser. No. 62/380,862, filed Aug. 29, 2016 and titled "Methods of Steering and Delivery of Intravascular Devices"; U.S. Provisional Patent Application Ser. No. 62/380,873, filed on Aug. 29, 2016 and titled "Multilumen Catheter"; U.S. Provisional Patent Application Ser. No. 62/380,888, filed Aug. 29, 2016 and titled "Methods, Systems, and Devices for Sealing and Flushing a Delivery System"; U.S. Provisional Patent Application Ser. No. 62/404,511, filed Oct. 5, 2016 and titled "Systems and Methods for Loading and Deploying an Intravascular Device"; U.S. Provisional Patent Application Ser. No. 62/422,426, filed on Nov. 15, 2016 and titled "Delivery Catheter Distal Cap"; U.S. Provisional Patent Application Ser. No. 62/430,143, filed on Dec. 5, 2016 and titled "Intravascular Device Delivery Sheath"; U.S. Provisional Patent Application Ser. No. 62/430,149, filed on Dec. 5, 2016 and titled "Systems and Methods for Loading and Deploying an Intravascular Device"; U.S. Provisional Patent Application Ser. No. 62/436,887, filed Dec. 20, 2016 and titled "Mechanical Interlock for Catheters"; U.S. Provisional Patent Application Ser. No. 62/436,913, filed on Dec. 20, 2016 and titled "Methods of Steering and Delivery of Intravascular Devices"; U.S. Provisional Patent Application Ser. No. 62/436,918, filed Dec. 20, 2016 and titled "Moveable Guidewire Lumen"; and U.S. Provisional Patent Application Ser. No. 62/436,926, filed Dec. 20, 2016 and titled "Methods, Systems, and Devices for Sealing and Flushing a Delivery System," the disclosures of which are incorporated herein by references in their entireties.

This application also claims the benefit of and priority to: U.S. Provisional Patent Application Ser. No. 62/436,985, filed on Dec. 20, 2016 and titled "Systems and Methods for Loading and Deploying an Intravascular Device"; U.S. Provisional Patent Application Ser. No. 62/436,922, filed Dec. 20, 2016 and titled "Systems and Methods for Loading and Deploying an Intravascular Device"; and U.S. Provisional Patent Application Ser. No. 62/462,776, filed on Feb. 23, 2017 and titled "Systems and Methods for Loading and Deploying an Intravascular Device."

BACKGROUND

1. Field of the Invention

The present disclosure generally relates to an implantable cardiac device. In particular, this disclosure describes devices, systems, and methods for delivering an intravascular device to targeted anatomy within the heart such as at the mitral annulus.

2. The Relevant Technology

Intravascular medical procedures allow the performance of therapeutic treatments in a variety of locations within a patient's body while requiring only relatively small access incisions. An intravascular procedure may, for example, eliminate the need for open-heart surgery, reducing risks, costs, and time associated with an open-heart procedure. The intravascular procedure also enables faster recovery times with lower associated costs and risks of complication. An example of an intravascular procedure that significantly reduces procedure and recovery time and cost over conventional open surgery is a heart valve replacement or repair procedure in which an artificial valve or valve repair device is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more deflecting mechanisms, which can be achieved by tension cable, or other mechanisms positioned inside the catheter. Precise control of the distal end of the catheter allows for more reliable and faster positioning of a medical device and/or implant and other improvements in the procedures.

An intravascularly delivered device needs to be placed precisely to ensure a correct positioning of the medical device, which is essential for its functionality, as the device may be difficult to reposition after the device is fully deployed from the delivery system. Additionally, the ability to recapture a partially deployed device is desirable in the event that the distal end of the catheter moves relative to the target location and compromises the precise positioning of the device.

BRIEF SUMMARY

The present disclosure describes devices, systems, and methods for intravascularly delivering an intravascular device to a targeted cardiac valve. In one embodiment, a delivery system for intravascularly delivering an intravascular device to a targeted cardiac valve includes a handle assembly and an elongated delivery member. The delivery member has a proximal end and a distal end. The proximal end of the delivery member is coupled to the handle assembly and the delivery member extends distally from the handle assembly to its distal end. The delivery member is configured to detachably couple to an implantable intravascular device at its distal end. The delivery member also includes an outer sheath having a cover configured to constrain and/or hold the intravascular device in a pre-deployed configuration, a steering component configured to curve the delivery member in a compound curve that enables intravascular delivery of the delivery member to the targeted cardiac valve, a delivery catheter configured to longitudinally translate the intravascular device relative to the outer sheath, and a suture catheter having one or more tethers configured to detachably couple to a proximal section of the intravascular device. The suture catheter is longitudinally translatable relative to the delivery catheter to enable adjustment of tension in the one or more tethers.

In some embodiments, the steering component is a steering catheter nested within the outer sheath. The steering catheter may include a plurality of tension cables and corresponding tension cable lumen, the tension cables providing for steering of the steering catheter by adjusting tension in the tension cables. The steering catheter may be formed as a hypotube, the hypotube having a cut pattern that increases the flexibility of the hypotube relative to an uncut section of hypotube. The steering catheter may include a plurality of microfabricated cuts along at least a proximal section of the distal piece, the microfabricated cuts being configured to provide bending in a single plane.

In some embodiments, the outer sheath includes a coil and a braided sleeve. The coil of the outer sheath may be formed from a coil wire having a "D" shaped cross section to provide a rounded inner surface. The outer sheath may include a fluid impermeable flexible polymer cover disposed over the coil and braided sleeve. In some embodiments, the distal piece of the outer sheath is rotationally decoupled from the remainder of the outer sheath. In some embodiments, the delivery catheter includes a compression coil at least at a distal section.

In some embodiments, the delivery system is supported by a fixture. The fixture includes a plurality of supports to support the outer sheath, a steering catheter handle, a delivery catheter holder, and a suture catheter holder. The fixture also includes one or more adjustable controls which enable movement of different components of the delivery member relative to other components of the delivery member. In some embodiments, the fixture includes a delivery device adjustor for longitudinally translating the entire delivery device relative to a base, an outer sheath adjustor for translating the outer sheath relative to other components of the delivery member, and a deployment adjustor for translating the delivery catheter, outer sheath, and suture catheter relative to the steering catheter. In some embodiments, the handle assembly includes a delivery catheter holder, a suture catheter holder, and a suture catheter adjustor, the suture catheter adjustor being coupled to the delivery catheter holder, and the suture catheter holder including threads which engage with corresponding threads of the suture catheter adjustor such that rotation of the suture catheter adjustor translates the suture catheter holder relative to the delivery catheter holder Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

In order to describe various features and concepts of the present disclosure, a more particular description of certain subject matter will be rendered by reference to specific embodiments which are illustrated in the appended drawings. Understanding that these figures depict just some example embodiments and are not to be considered to be limiting in scope, various embodiments will be described and explained with additional specificity and detail through the use of the accompanying drawings in which:

FIGS. 5A and 5B illustrate operation of the handle assembly to translate the outer sheath of the delivery member relative to other components of the delivery member;

FIGS. 6A and 6B illustrate operation of the handle assembly to translate the outer sheath, the delivery catheter, and the suture catheter relative to the steering catheter of the delivery member;

FIGS. 7A and 7B illustrate operation of the handle assembly to translate the suture catheter relative to the delivery catheter;

FIGS. 8A and 8B illustrate operation of the handle assembly to translate the guidewire tube relative to the suture catheter;

DETAILED DESCRIPTION

Delivery System Overview

The present disclosure is directed to devices, systems, and methods for delivering an implantable intravascular device to targeted intravascular anatomy, including a targeted cardiac valve. Suitable intravascular devices that may be utilized in conjunction with the delivery system embodiments described herein may include valve repair devices, annuloplasty devices, valve clip devices, artificial heart valve devices, and other interventional devices.

Figure 1:
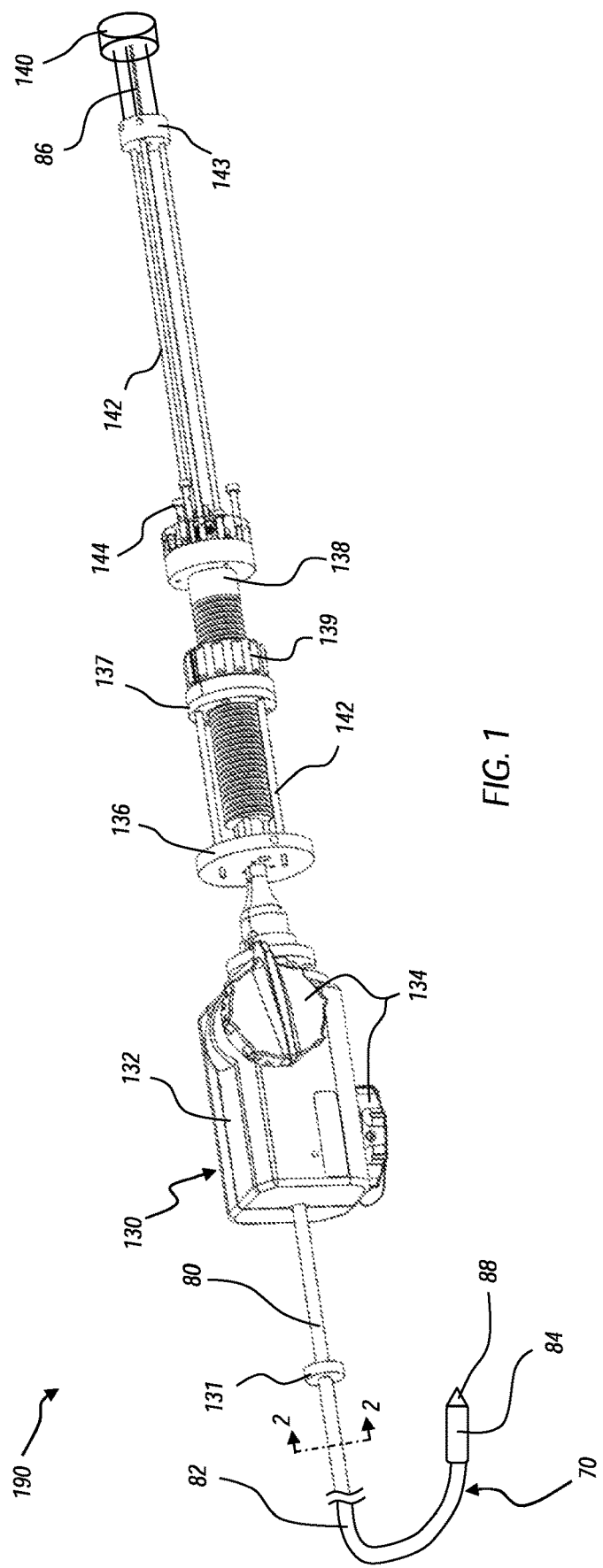
FIG. 1 illustrates a delivery system configured for delivering, positioning, and deploying an intravascular device, the delivery system including a handle assembly coupled to a delivery member.

FIG. 1 illustrates an embodiment of a delivery system 190. As shown, the delivery system 190 includes a handle assembly 130 and an elongated delivery member 70 (also referred to herein as simply the elongated member or the delivery member). The delivery member 70 is coupled to the handle assembly 130 and extends distally from the handle assembly 130. The delivery member 70 includes a plurality of catheter and/or hypotube members which provide different functionality during operation of the delivery system 190 to enable effective delivery and deployment of an intravascular device.

The proximal end of an outer sheath 82 (also referred to herein as delivery sheath 82) is coupled to an end ring 131, and the outer sheath 82 extends to a distal end where it is coupled to a distal piece 84. The distal piece 84 functions to house an intravascular device in a compressed, pre-deployed state during intravascular delivery of the device to the targeted cardiac site. A steering catheter handle 132 is disposed proximal of the end ring 131. The proximal end of a steering catheter 80 is coupled to the steering catheter handle 132, and the steering catheter 82 extends distally from the steering catheter handle 132 into the outer sheath 82. The steering catheter handle 132 includes one or more controls 134 which are operatively coupled to the steering catheter so that manipulation of the controls 134 adjusts the curvature of the steering catheter 80. Because the steering catheter 80 is nested within the outer sheath 82, curving of the steering catheter 80 causes corresponding curving/steering in the outer sheath 82. The illustrated embodiment of the delivery member 70 includes additional components which are not visible in the view of FIG. 1 but may be seen in the cross-sectional view of FIG. 2.

Figure 2:
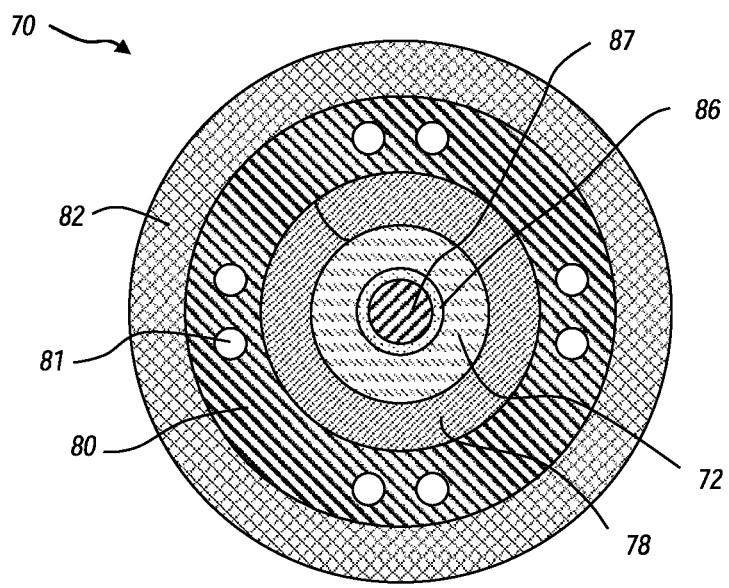
FIG. 2 illustrates a cross-section of the delivery member, showing various nested components of the delivery member, including an outer sheath, a steering catheter, a delivery catheter, a suture catheter, and a guidewire tube.

FIG. 2 illustrates a cross-sectional view of the delivery member 70 taken along the cross-section line 2-2. As shown, the steering catheter 80 is disposed within the outer sheath 82. A delivery catheter 78 is disposed within the steering catheter 80. A suture catheter 72 is disposed within the delivery catheter 78, and a guidewire tube 86 is disposed within the suture catheter 72. The guidewire tube 86 is configured for receiving a guidewire 87. Additional structural details and related functionality of these components will be described in more detail below. Although the particular nested configuration shown in FIG. 2 represents one preferred embodiment, alternative embodiments may include a different concentric arrangement of constituent parts. For example, some embodiments may configure the outermost member with steering functionality, some embodiments may include more than one catheter with steering functionality, some embodiments may trade the radial positions of the suture catheter 72 and delivery catheter 78, etcetera.

The steering catheter 80 includes a plurality of lumens 81 extending through the length of the steering catheter 80. As explained in more detail below, the lumens 81 may be configured for receiving tension cables which extend between the controls 134 and the distal end of the steering catheter 80. One or more tension cables may additionally or alternatively be coupled to intermediate sections of the steering catheter 80. Manipulation of the controls 134 therefore adjusts tension in the tension cables to increase or decrease curvature of the steering catheter 80 at various positions. Although the controls 134 are shown here as knobs, alternative embodiments may additionally or alternatively include one or more buttons, sliders, ratcheting mechanisms, or other suitable controls capable of adjusting tension to provide steering. Illustrative structures that can be used as part of the steering catheter handle 132 and or steering catheter 80 are described in U.S. Pat. No. 7,736,388, the disclosure of which is incorporated herein by this reference.

Referring again to FIG. 1, a delivery catheter holder 136 is disposed proximal of the steering catheter handle 132. Although not visible in the view of FIG. 1, the proximal end of the delivery catheter 78 is coupled to the delivery catheter holder 136. The delivery catheter 78 extends distally away from the delivery catheter holder 136 and into the steering catheter 80. A suture catheter holder 138 is disposed proximal of the delivery catheter holder 136. The suture catheter 72 may be coupled to the suture catheter holder 138 so that translation of the suture catheter holder 138 corresponds to movement of the suture catheter 72. For example, the suture catheter 72 may be selectively locked relative to the suture catheter holder 138 through a set screw, clamp, or other selective holding mechanism. The suture catheter 72 extends distally away from the suture catheter holder 138 and into the delivery catheter 78.

An alignment ring 137 and alignment rods 142 provide structural support for maintaining proper alignment of the delivery catheter holder 136 and suture catheter holder 138, which thereby functions to maintain coaxial alignment of the delivery catheter 78 and suture catheter 72. A suture catheter control 139 is coupled to the alignment ring 137 and is operatively coupled to the suture catheter holder 138. Manipulation of the suture catheter control 139 adjusts the relative positioning of the delivery catheter holder 136 and suture catheter holder 138. In the illustrated embodiment, the suture catheter control 139 operates through threaded engagement with the suture catheter holder 138, such that rotation of the suture catheter control 139 translates the suture catheter holder 138 relative to the control 139 and therefore relative to the delivery catheter holder 136. Alternative embodiments may additionally or alternatively include one or more of a slider and rail assembly, a ratcheting mechanism, or other suitable means of linear adjustment.

A second set of alignment rods 142 extend proximally from the suture catheter holder 138 and to a suture catheter cap 143. The suture catheter 72 may extend proximally to and be attached to the suture catheter cap 143. By decoupling the suture catheter 72 from the suture catheter holder 138, a user may advance and retract the suture catheter 72 by sliding/translating the suture catheter cap 143 along the alignment rods 142. The guidewire tube 86 extends distally through the alignment cap 143 and into the suture catheter 72 at the suture catheter holder 138. The guidewire tube 86 extends to the distal end of the delivery member 70 where it is attached to a distal tip 88. The distal tip 88 is preferably formed from a flexible polymer material and provides an angled, atraumatic shape which assists in passing the delivery member 70 across the inter-atrial septum to the mitral annulus, which is required in a typical intravascular approach such as a transfemoral approach.

The guidewire tube 86 may be selectively translatable relative to the suture catheter cap 143, so that the guidewire tube 86 and distal tip 88 may be linearly translated relative to the suture catheter 72. In the illustrated embodiment, the guidewire tube 86 is coupled to a guidewire tube handle 140. The guidewire tube 86 may be selectively locked in longitudinal position relative to the suture catheter holder 138 and/or suture catheter cap 143, such as through a set screw, clamp, or other selective fastener. For example, such a fastening structure may be associated with the suture catheter cap 143.

When the guidewire tube 86 is linearly locked to the suture catheter cap 143, the guidewire tube 86 will longitudinally translate with the delivery catheter handle 138 and/or suture catheter cap 143. The distal tip 88 and suture catheter 72 will thus move together. When unlocked, the guidewire tube 86 (and likewise the distal tip 88) may be moved relative to the suture catheter 72. As described in more detail below, the ability to retract the distal tip 88 relative to the suture catheter 72 reduces the risk that the distal tip 88 will become overextended during deployment, where it could become tangled in chordae tendineae and/or cause injury to cardiac tissue.

The illustrated suture catheter holder 138 also includes a set of tensioner posts 144. In some embodiments, sutures may extend from the distal end of the suture catheter 72 to the tensioner posts 144. The sutures may be wrapped around respective tensioner posts 144 such that screwing/unscrewing of the tensioner posts 144 adjusts tension of the coupled sutures. However, in other embodiments, sutures do not pass entirely to the proximal handle assembly 130 and the tensioner posts 144 may be omitted.

Figure 3:
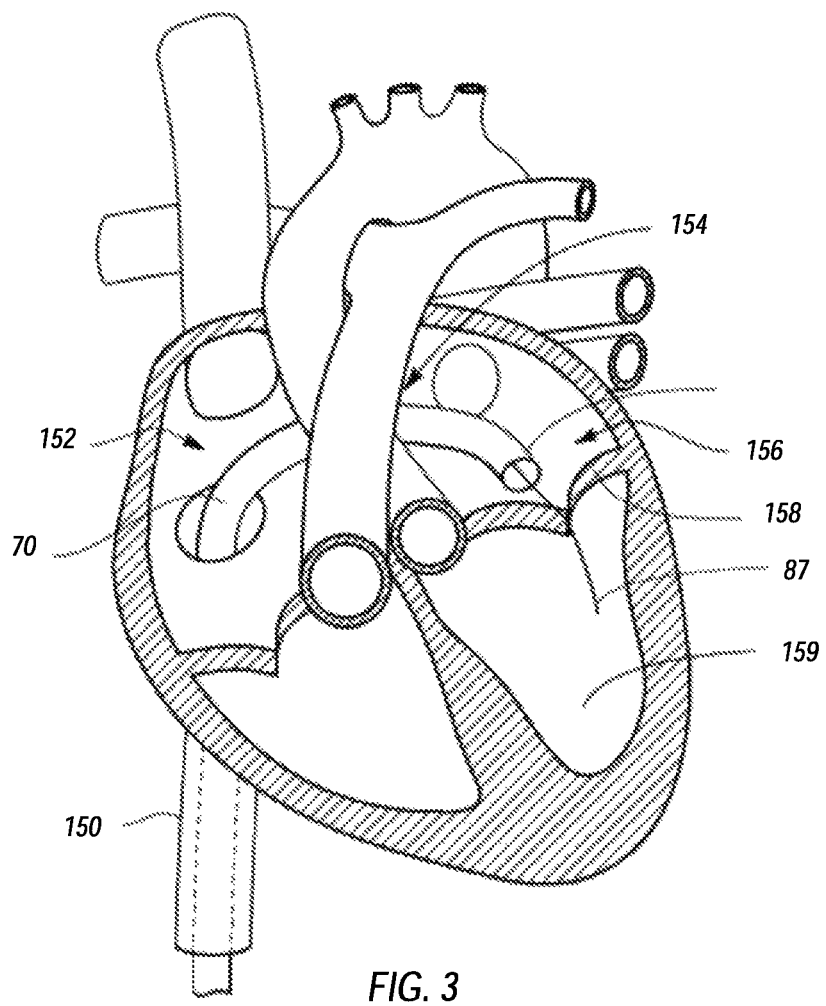
FIG. 3 illustrates an exemplary approach for delivering an intravascular device to the mitral annulus.

FIG. 3 illustrates a schematic representation of a patient's heart and a delivery procedure that may be conducted using the illustrated delivery system 190. The delivery member 70 may be inserted into the patient's vasculature (e.g., through a transfemoral approach) and directed to the inferior vena cava 150. The delivery member 70 is passed through the inferior vena cava 150 toward the heart. Upon entering the heart from the inferior vena cava 150, the delivery member 70 enters the right atrium 152. For mitral valve related procedures, the delivery member 70 must further pass into the left atrium 156 by passing through a puncture in the intra-atrial septum 154.

In other implementations, such as for procedures associated with a tricuspid valve, the delivery member 70 may be passed through the inferior vena cava 150 and into the right atrium 152, where it may then be positioned and used to perform the procedure related to the tricuspid valve. As described above, although many of the examples described herein relate to delivery to the mitral valve, one or more embodiments may be utilized in other cardiac procedures, including those involving the tricuspid valve.

Although a transfemoral approach for accessing a targeted cardiac valve is one preferred method, it will be understood that the embodiments described herein may also be utilized where alternative approaches are used. For example, embodiments described herein may be utilized in a transjugular approach, transapical approach, or other suitable approach to the targeted anatomy. For procedures related to the mitral valve or tricuspid valve, delivery of the replacement valve or other interventional device is preferably carried out from an atrial aspect (i.e., with the distal end of the delivery member 70 positioned within the atrium superior to the targeted valve). The illustrated embodiments are shown from such an atrial aspect. However, it will be understood that the interventional device embodiments described herein may also be delivered from a ventricular aspect.

In some embodiments, a guidewire 87 is utilized in conjunction with the delivery member 70. For example, the guidewire 87 (e.g., 0.014 in, 0.018 in, 0.035 in) may be routed through the guidewire tube 86 of the delivery member 70 to the targeted cardiac valve.

Operation of the Handle Assembly

Figure 4:
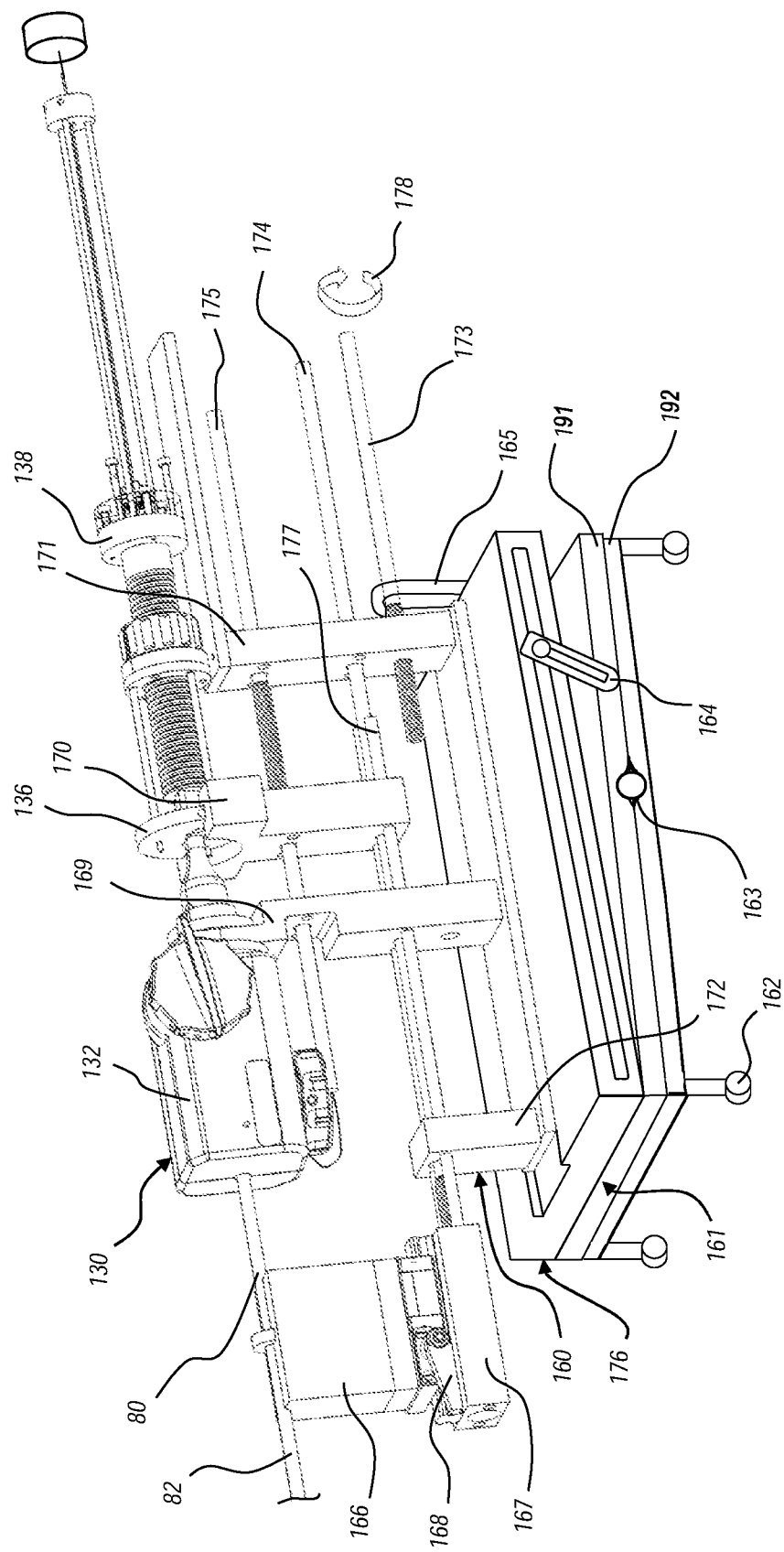
FIG. 4 illustrates an embodiment of a fixture configured for supporting the delivery system, the fixture including a stabilizer and a base.

FIG. 4 illustrates the handle assembly 130 positioned on a fixture 176. The fixture 176 includes a stabilizer 160 which supports the handle assembly 130 and provides adjustment of various components of the handle assembly 130. The fixture 176 also includes a base 161 configured to support the stabilizer 160 and handle assembly 130, and to provide the ability to adjust the position of the entire handle assembly 130. The base 161 may include wheels 162 for moving and positioning of the assembly. The base 161 also includes an angular adjuster 164 configured for adjusting the angle of the handle assembly 130 by lifting or lowering the upper section of the base 161. The base 161 further includes a slider lock 163. Unlocking of the slider lock 163 allows a user to slide an upper section 191 of the base forward or backward relative to a lower section 192 of the base in order to selectively advance or retract the delivery system.

The fixture 176 may also include a base bearing 165 connected to the base 160 and to a stabilizer adjustor 173. The base bearing 165 allows the stabilizer adjustor 173 to rotate but prevents linear movement of the stabilizer adjustor 173 relative to the base bearing 165. The stabilizer adjustor 173 includes threads which engage with corresponding threads of a proximal support 171 of the stabilizer 160. The proximal support 171 is mechanically connected to a steering catheter handle support 169 and a distal support 172. Rotation of the stabilizer adjustor 173, as shown by arrow 178, thus causes the entire stabilizer 160 to translate relative to the base 161. For example, rotation of the stabilizer adjustor 173 in one direction will advance the stabilizer 160 (and handle assembly 130 with it) while rotation in the opposite direction will retract.

The illustrated fixture 176 is therefore configured to provide dual-mode translation of the delivery system. For example, manipulation of the slider lock 168 may be utilized for translational adjustments of the delivery system on a relatively more macro level, while manipulation of the stabilizer adjustor 173 may be utilized for finer translational adjustments on a relatively more micro level. The combination of both modes of translation beneficially combines the ability for rapid adjustment across longer translational movements with the ability for fine adjustment where more precise movements are required or preferred.

The stabilizer 160 includes additional components configured to provide adjustment of the different components of the handle assembly 130. The outer sheath 82 is supported by an outer sheath support 166. The outer sheath support 166 is disposed upon a slider block 167. The outer sheath support 166 can be selectively translated upon the slider block 167 to translate the outer sheath 82 relative to the other components of the delivery member 70. A slider lock 168 can lock the position of the outer sheath support 166 upon the slider block 167 to prevent translation via sliding.

The steering catheter handle 132 is supported by the steering catheter handle support 169, and the delivery catheter holder 136 is supported by a delivery catheter support 170. The proximal support 171 supports the suture catheter holder 138. An outer sheath adjustor 174 and a deployment adjustor 175 enable additional operation of the delivery device, as described in more detail below. As shown, connecting rods 177 are attached to the delivery catheter support 170, pass slidably through the steering catheter handle support 169 and the distal support 172, and attach to the sliding block 167. Translation of the delivery catheter support 170 may therefore be coupled to translation of the outer sheath support 166 in some circumstances.

FIGS. 5A and 5B illustrate in greater detail operation of the handle assembly for translating the outer sheath 82. Sheath movement may be utilized to deploy an intravascular device sheathed at or otherwise attached to the distal end of the outer sheath 82, or to recapture such an intravascular device by advancing the outer sheath 82 over the device. The illustrated embodiment provides two modes for translating the outer sheath 82. The outer sheath adjustor 174 and the slider block 167 are coupled to each other with corresponding threads, and rotation of the outer sheath adjustor 174 causes the slider block 167 to translate. With the slider lock 168 engaged, the outer sheath support 166 and outer sheath 82 move with the slider block 167. The slider lock 168 may also be disengaged, allowing the outer sheath support 166 and outer sheath 82 to be manually advanced or retracted by sliding relative to the slider block 167.

As shown by corresponding arrows 180, rotation of the outer sheath adjustor 174 in one direction causes the slider block 167 to advance, and as shown by corresponding arrows 181, rotation of the outer sheath adjustor 174 in the opposite direction causes the slider block 167 to retract. In FIG. 5A, the slider lock 168 is in an engaged position. In FIG. 5B, arrows 182 show disengagement of the slider lock 168 and translation of the outer sheath support 166 upon the slider block 167. The dual mode adjustment of the outer sheath 82 beneficially allows a user to make different types of adjustments depending on procedural circumstances and/or preferences. For example, a user may make larger, quicker adjustments by unlocking the slider lock 168 and manually sliding the outer sheath support 166, and may make finer, more controlled adjustments by rotation of the outer sheath adjustor 174.

FIGS. 6A and 6B illustrate a deployment adjustment that moves several of the delivery member components relative to the steering catheter 80. FIG. 6A illustrates, by arrows 183, rotation of the deployment adjustor 175 in a first direction to retract the slider block 167, deployment catheter holder 136, and suture catheter holder 138. FIG. 6B illustrates, by arrows 184, rotation of the deployment adjustor 175 in a second direction to advance the slider block 167, deployment catheter holder 136, and suture catheter holder 138. As explained below, after the steering catheter 80 has been curved to orient the delivery member 70 with respect to the mitral annulus, the other components of the delivery member 70 will need to be advanced over the steering catheter 80 to move into a proper position for deployment of the intravascular device. Holding the steering catheter 80 in place while the other components are advanced allows the compound curve of the steering catheter 80 to remain in the desired position.

The deployment adjustor 175 is threadedly engaged with the delivery catheter support 170. The connecting rods 177 mechanically link the delivery catheter support 170 to the slider block 167. The connecting rods 177 are able to freely pass through the steering catheter handle support 169 without engaging. The delivery catheter holder 136 and the suture catheter holder 138 are also mechanically linked by way of the alignment ring 137 and suture catheter control 139. Accordingly, rotation of the deployment adjustor 175 causes the delivery catheter holder 136, slider block 167, and suture catheter holder 138 to translate while the position of the steering catheter handle 132 is maintained. Translation of the outer sheath support 166 can be assured by locking to the slider block 167.

FIGS. 7A and 7B illustrate an operation for moving the suture catheter holder 138 relative to the delivery catheter holder 136. FIG. 7A shows, by arrows 185, that rotation of the suture catheter control 139 in a first direction causes the suture catheter holder 138 to advance relative to the delivery catheter holder 136. FIG. 7B shows, by arrows 186, that rotation of the suture catheter control 139 in a second direction causes the suture catheter holder 138 to retract relative to the delivery catheter holder 136. The threaded engagement of the suture catheter control 139 to the suture catheter holder 138 allows for finely controlled adjustments of the suture catheter position. As explained in more detail below, sutures of the suture catheter 72 may be coupled to an intravascular device while the device is in a pre-deployed state, and movement of the suture catheter 72 relative to the delivery catheter 78 allows tension of the sutures to be adjusted.

FIGS. 8A and 8B illustrate an operation for moving the guidewire tube 86 and guidewire tube holder 140 relative to the other components of the delivery member 70. FIG. 8A shows, by arrows 187, retraction of the guidewire tube holder 140 and corresponding retraction of the distal tip 88. FIG. 8B shows, by arrows 188 advancement of the guidewire tube holder 140 and corresponding advancement of the distal tip 88. The ability to adjust the distal tip 88 can lower the risk that the distal tip 88 undesirably interferes with chordae tendineae or other cardiac anatomy during deployment procedures. For example, during deployment of an intravascular device, the suture catheter 72 may be advanced to disengage from the intravascular device. If the distal tip 88 is not retracted relative to the advancing suture catheter 72, the distal tip 88 could extend too far into the ventricle where it could catch chordae tendineae and/or impinge against the cardiac wall.

Additional Details of Elongated Member Components

Figure 9:
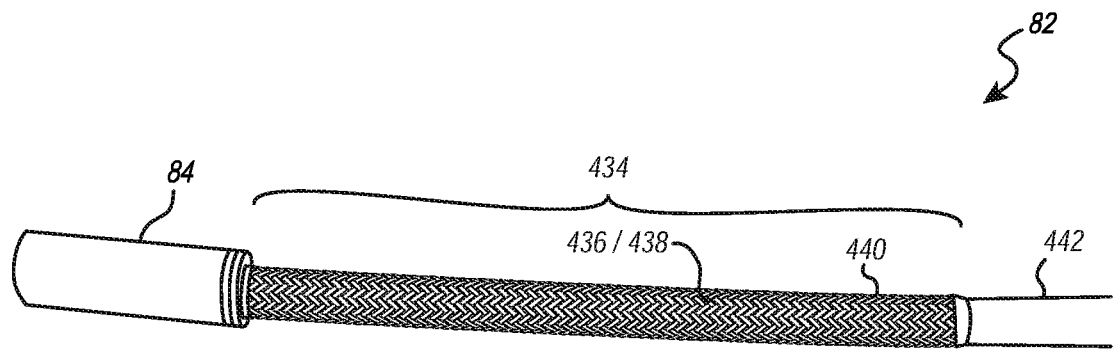
FIG. 9 illustrates the outer sheath, showing various sections that may be formed in the outer sheath.
Figure 10:
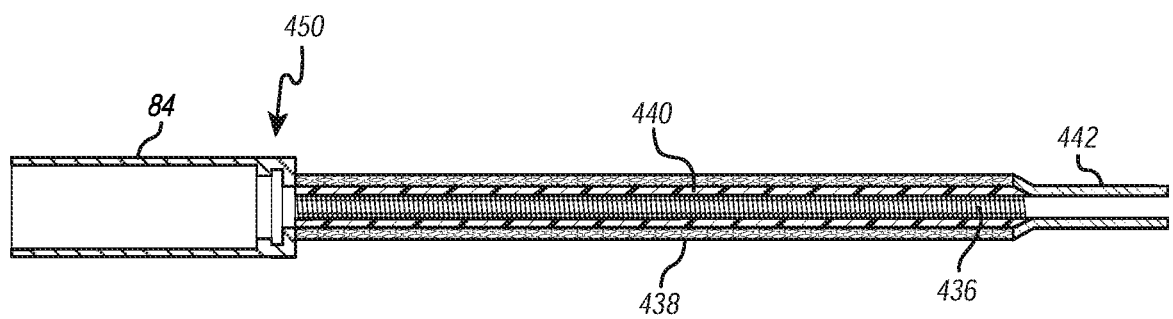
FIG. 10 is a cross-sectional view of FIG. 9.

FIGS. 9 and 10 illustrate a portion of the distal end of the outer sheath 82 and distal piece 84. Distal piece 84 can be made of a steel cylindrical tube having an inner diameter and length sized to receive the intravascular device, in a collapsed/pre-deployed configuration, within the lumen of distal piece 84. Distal piece 84 can include a plurality of microfabricated cuts (e.g., laser cuts) and a pair of continuous longitudinal spines located on opposite sides so that cover can bend and flex substantially in a single plane. The outer sheath 82 can also include a bending portion 434 that can be attached to and located proximal to distal piece 84. Bending portion 434 can preferably have a sufficient length to surround and extend along that portion of the delivery system that is designed bend and reorient, via the steerable catheter 80, to navigate through a patient's vasculature and/or heart to a target site for deploying the intravascular device. In some embodiments, the bending portion 434 can include a cable tube or coil 436 surrounded by a braided structure 438 (sometimes collectively referred to as the "coil/braid portion 436/438") as shown in FIG. 11A.

Figure 11A:
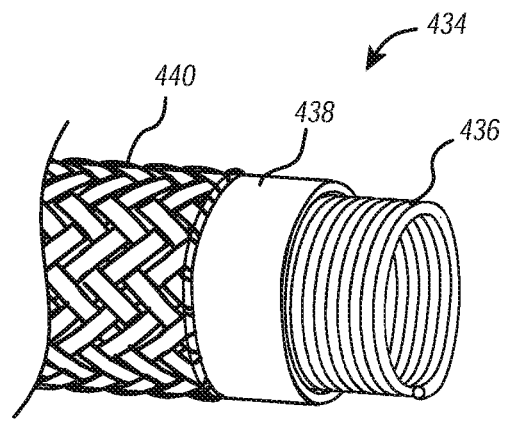
FIG. 11A is a partial cut-away view of an intermediate portion of the delivery sheath.

FIG. 11A is a perspective cutaway view of the sheath 82. As shown, the sheath 82 may have an inner cable tube or coil 436 and an outer braided sleeve or structure 438. Coil 436 can be made of or include a resilient coil material. For example, the coil material may be stainless steel, nickel titanium (e.g., Nitinol), other metal alloy, a thermoplastic, other polymers such as PEEK, ceramics, carbon tubing, glass, or combinations thereof. In at least one embodiment, coil 436 can be a stainless steel coil that has a droop value of 11:1 or higher. Coil 436 can be sized relative to the braided structure 438 such that the coil 436 has an outer diameter ("OD") in a relaxed state that is substantially the same as an inner diameter ("ID") of braided structure 438 in a relaxed state.

Figure 11B:
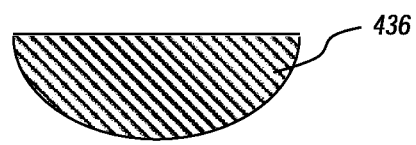
FIG. 11B is a side view of the coil of the intermediate portion of the sheath shown in FIG. 11A.

In preferred embodiments, the coil 436 has an inner surface sufficiently smooth to allow the outer sheath 82 to effectively move over the steering catheter 80 and/or delivery catheter 78. For example, as shown in FIG. 11B, the wire forming the coil 436 may have a "D" cross-sectional shape or other rounded shape such that the inward facing side is curved to minimize interference with other components translating within the coil 436.

Figure 11C:
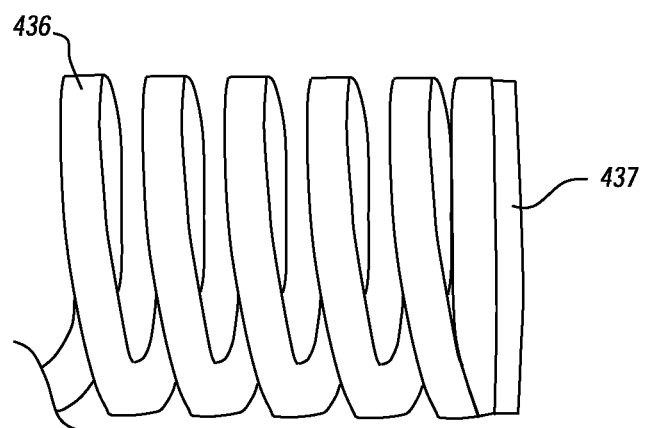
FIG. 11C is a cross-sectional view of one exemplary configuration of a wire for forming the coil of FIG. 11B.

FIG. 11C shows another view of the coil 436 showing a coil end 437 (which may represent a proximal end and/or a distal end). As shown, the coil end 437 is formed with a fully closed circumference. This allows the coil end 437 to more readily welded, adhered, or otherwise attached to a connecting ring or hypotube section of the elongated member 70. For example, the closed coil construction of the coil end 437 allows a laser weld to cover the full 360-degree circumference of the coil end 437.

In some embodiments, braided sleeve 438 may include a plurality of threads or fibers that are woven together. For example, braided sleeve 438 may include a plurality of threads that extend at an angle to one another and are woven together in a repeating pattern. The plurality of threads may be woven in a diamond two wire two-under-two, over-two pattern; a half-load single wire over-one, one-under pattern; a full-load single wire over-two, under-two pattern; other alternating woven patterns; or combinations thereof. In other embodiments, braided sleeve 438 may include a single thread routed substantially straight longitudinally through the plurality of threads.

The threads may be round threads, elliptical threads, or flat threads. The threads may be made of or include a variety of reinforcement materials, such as, metals, metal alloys, thermoplastics, other polymers, ceramics, glasses or combinations thereof. In some embodiments, the reinforcement material or materials may have a greater elastic modulus than the body material. For example, a braided sleeve may include a mixture of threads with different properties, such as stainless steel threads woven with polymer threads. In at least one embodiment, braided sleeve 438 may include a plurality of 304 stainless steel wires woven in a diamond pattern. Such an embodiment of a braided sleeve may include between 16 and 72 threads of stainless steel. For example, braided sleeve 438 may include 24 strands, with each strand consisting of four wires.

Coil 436 and braided sleeve 438 may be longitudinally fixed to one another at or near a proximal end of the outer sheath 82 and at or near the distal end of the outer sheath 82. In some embodiments, the braided sleeve 438 may be welded or soldered to the coil 436 at a proximal end and at a distal end of the outer sheath 82. In other embodiments, the braided sleeve 438 may be fixed to the coil 436 with an adhesive at a proximal end and a distal end of the outer sheath 82. In yet other embodiments, the braided sleeve 438 may be fixed to the coil 436 via an intermediate element (e.g., an annular end cap) at a proximal end and a distal end of the outer sheath 82. In yet other embodiments, braided sleeve 438 and coil 436 may be longitudinally fixed relative to one another at one or more points between a proximal end and a distal end of the outer sheath 82. For example, braided sleeve 438 and the coil 436 may be longitudinally fixed relative to one another at a centerpoint.

Referring again to FIGS. 9 and 10, attached to the proximal end of bending portion 434 is a cut hypotube 442 that extends from bending portion 434 to the proximal end of the sheath 82. Hypotube 442 can include a plurality of slits and at least one longitudinally continuous spine that can preferably be continuous and uninterrupted along a longitudinal length of, and located at a fixed angular location on, hypotube 442.

In some embodiments, the longitudinally continuous spine of hypotube 442 may allow the sheath 82 to transmit tension force applied at a proximal end of the sheath 82 to a distal end of the sheath 82 without substantial elongation of the sheath 82. In other embodiments, the longitudinally continuous spine hypotube 442 may allow the sheath 82 to transmit compression force applied at a proximal end to the distal end without substantial shortening of the sheath 82. For example, some embodiments of a sheath may exhibit a change in a longitudinal length of less than 30% during application of a compression force of 40 pounds (177.9 Newtons) or greater and/or application of a tension force of 40 pounds (177.9 Newtons) or greater.

In other examples, some embodiments of a sheath may exhibit a change in a longitudinal length of less than 5% during application of a compression force of 40 pounds (177.9 Newtons) or greater and/or a tension force of 40 pounds (177.9 Newtons) or greater. In yet other examples, some embodiments may exhibit a change in a longitudinal length of less than 2% during application of a compression force of 40 pounds (177.9 Newtons) or greater and/or a tension force of 40 pounds (177.9 Newtons) or greater.

In some embodiments, the outer sheath 82 may transmit tension force without substantial change to the longitudinal length of the delivery sheath and may foreshorten by 5%, 10%, 15%, 20%, 25%, 30%, 40%, 50%, 75%, 100%, 150%, 200%, 250%, 300%, 350%, 400% or any value therebetween during compression. In at least one embodiment, the coil 436 may compress by a percentage of the initial longitudinal length of the sheath 82 before the coils contact one another and the coil 436 transmits compression forces along the longitudinal length thereof. For example, the coil rings may have an initial (i.e., non-stressed) spacing of between 0.1 mm and 5.0 mm, between 1 mm and 4 mm, between 2 mm to 3 mm, or any values therebetween to provide a bending radius to navigate the anatomy toward and into a patient's heart.

In such embodiments, it can be desirable for the bending portion 434 of delivery catheter to remain liquid tight. To seal the bending portion 434, a flexible, fluid impermeable covering can be provided over the coil/braid portion 436/438, extending from the distal piece 84 to a location proximal the coil/braid portion 436/438. For example, the delivery sheath 82 can also include a thin walled flexible cover 440 that extends from the distal piece 84 to the hypotube 442. Flexible cover 440 can be bonded at each end to the underlying structure, using one of a variety of different adhesives, thermal adhesives, UV bonded adhesive, or other techniques. Flexible cover 440 can be fabricated from Pelathane 80A, Tecoflex 72A, Texin 70A, Chronoflex 45D, or other suitable flexible material. Flexible cover 440 can also be coated with hydrophilic coating. The wall thickness of flexible cover 440 could be between 0.001" to 0.006" and preferably between 0.002" to 0.004", and could have a diameter smaller than an outer diameter of the coil/braid portion 436/438.

Flexible cover 440 can be bonded at its distal end to a proximal end portion of distal piece 84 and can be bonded at is proximal end to a distal end portion of hypotube 442. An intermediate portion of flexible cover 440, including that portion that extends over the flexible coil/braid portion 436/438, is not bonded to flexible coil/braid portion 436/438, but rather can preferably be press fit or otherwise able to move relative to, and stretch over, flexible coil/braid portion 436/438. Flexible cover 440 can preferably be made of a material with some elasticity and can be attached at opposing ends to underlying structure in a way that it is stretched and normally retains some tension, which can help avoid wrinkles forming in flexible cover 440 when the delivery sheath 82 is bent or otherwise flexed. When flexible cover 440 is stretched onto the coil/braid portion 436/438 during fabrication, flexible cover 440 can foreshorten by up to 20%, but can easily stretch so as not to impair the flexibility of coil/braid portion 436/438.

During delivery, coil/braid portion 436/438 can be stretched to the point where the braided structure 438 locks down on the coil 436 and can transmit high tension forces that may be needed to retract the outer sheath and distal piece 84 from the intravascular device. Conversely, if recapture of the intravascular device should become necessary, having the coil/braid portion 436/438 under a certain amount of compression in some circumstances can also provide an advantage. The stretching of flexible cover 440 also accommodates these relative movements of coil 436 and braided structure 438 within coil/braid portion 436/438.

To facilitate fabrication, a mandrel can be disposed within the lumen of the delivery sheath 82, thereby stiffening delivery sheath 82, so that flexible cover 440 can be stretched and/or rolled over coil/braid portion 436/438, and then the opposing ends of flexible cover 440 can be sealed to the underlying structure.

Referring again to FIG. 10, delivery sheath 82 can also be coupled to distal piece 84 via a swivel connection, generally indicated at 450. To overcome the challenging forces that can develop during insertion of a relatively large delivery catheter into the vasculature of a patient, swivel connection 450 allows rotation of delivery sheath 82 by a few degrees, back and forth (i.e., alternating between clockwise rotation and counter-clockwise rotation) while at the same time moving the delivery system 400 in a generally longitudinal direction. This rotational motion (during simultaneous longitudinal translation) helps to overcome some of the longitudinal forces that may resist insertion of delivery sheath 82 through a patient's vasculature.

However, in some embodiments the intravascular device can be positioned within and covered by the distal piece 84 and can also be connected to the delivery catheter within the delivery system. Therefore, it might be desirable for an intermediate portion of the delivery sheath 82 (such as bending portion 434 and hypotube 442) to be free to swivel relative to the intravascular device and distal piece 84 while maintaining the intravascular device in stable and proper alignment with the delivery catheter 76.

To facilitate this, the distal piece 84 can be rotationally decoupled from distal end of the delivery sheath 82 by providing a swivel connection between a proximal end portion of distal piece 84 and the distal end portion of delivery sheath 82. In the embodiment shown in FIG. 10, a first swivel connection 450 can be formed between the proximal end of distal piece 84 and the distal end of bending portion 434. For example, first swivel connection 450 can consist of an enlarged annular flange 452 welded to the distal end of the coil/braided sleeve 436/438, and flange 452 can be interposed between a pair of annular rings or ridges 454*a* and 454*b* formed on an inner surface of distal piece 84 at its proximal end. These structures cooperate to rotationally decouple the distal piece 84 from the bending portion 434, but at the same time maintain coupling between these elements in terms of longitudinal movement.

While the illustrated embodiment uses cooperating flanges, rings and/or ridges, other suitable elements can also be used to accomplish the same functions, including, but not limited to rings, welds, detents, or other suitable structures. The first swivel connection 450 can also include one or more o-rings or other sealing components (not shown) positioned between the cooperating elements of the swivel to provide a fluid-tight swivel connection. A second embodiment of first swivel connection 450 is illustrated in FIG. 12.

Figure 12:
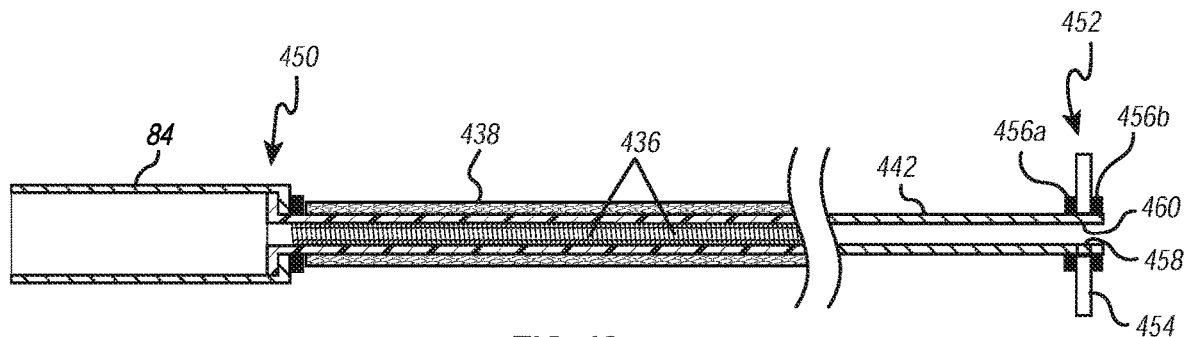
FIG. 12 is a cross-sectional view showing swivel connections between a distal piece and the delivery sheath and between the delivery sheath and a portion of the fixture.

Similarly, as further illustrated in FIG. 12, a second swivel connection 452 can also be formed at the proximal end of the sheath to rotationally decouple the delivery sheath 82 from the control fixture 454 (shown schematically only). Second swivel connection 452 can include a pair of spaced-apart, annular ridges 456*a* and 456*b* formed on the exterior surface and adjacent to the proximal end of hypotube 442. Annular ridges 456*a* and 456*b* form an annular recess 458 between which a complementary aperture 460 formed in fixture 454 can be positioned. Second swivel connection 452 can also include one or more o-rings or other sealing components (not shown) positioned between the cooperating elements of the swivel to provide a fluid-tight swivel connection.

Figure 13:
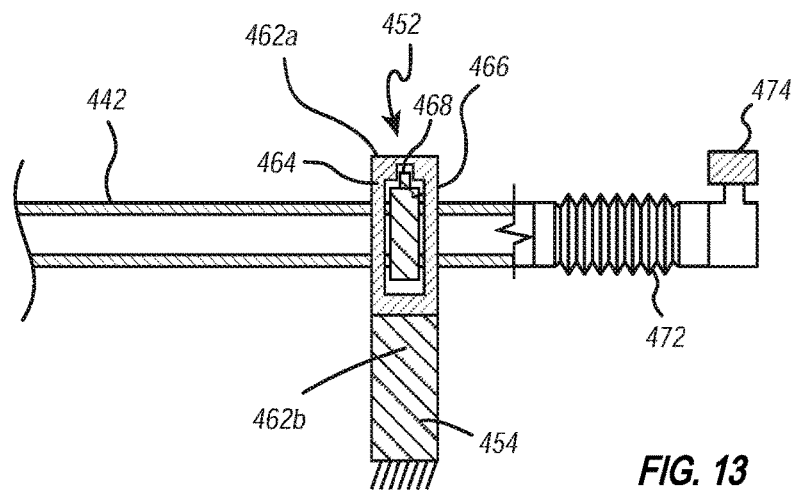
FIGS. 13 and 14 are cross-sectional views of an alternate embodiment of a swivel connection between the delivery sheath and the fixture.
Figure 14:
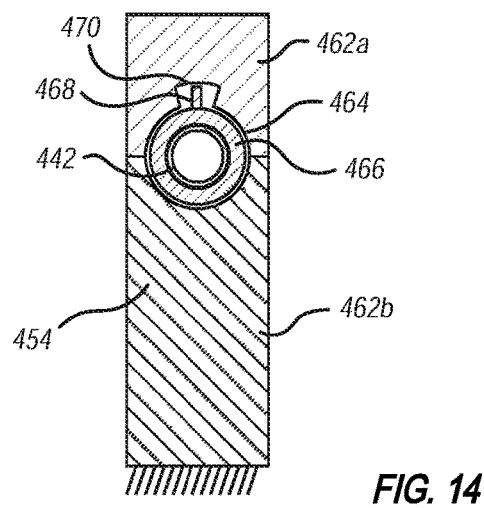

A second embodiment of second swivel connection 452 is illustrated in FIG. 13. In this embodiment, fixture 454 can provide a two-piece clamp 462*a* and 462*b* that includes an annular recess 464 that receives an annular ring 466 formed on the exterior of hypotube 442 at its proximal end. Ring 466 can easily be welded to the proximal end of hypotube 442. As further shown in FIG. 14, the ring can also have a pin 468 that extends into a complementary groove 470 formed in clamp 462. Pin 468 and groove 470 cooperate to limit rotation of ring 466 relative to clamp 462 within a predetermined swivel angle range (e.g., between plus and minus 15°), but any swivel angle can be accommodated by simply extending or reducing the length of groove 470.

As further illustrated in FIG. 13, an elastic bellow 472 can also be provided at the proximal end of hypotube 442. Bellow 472 allows a water tight connection, while at the same time accommodating rotational movement of hypotube 442. In addition, bellow 472 can stretch or compress when the delivery sheath 82 is moved longitudinally in a distal or proximal direction, as necessary, during delivery, deployment and/or release of the intravascular device. Finally, a standard luer lock connection 474 can be provided at the proximal end of bellow 472 to facilitate flushing of the interstitial spaces within delivery sheath 82 in preparation for an intervascular procedure.

Figure 15:
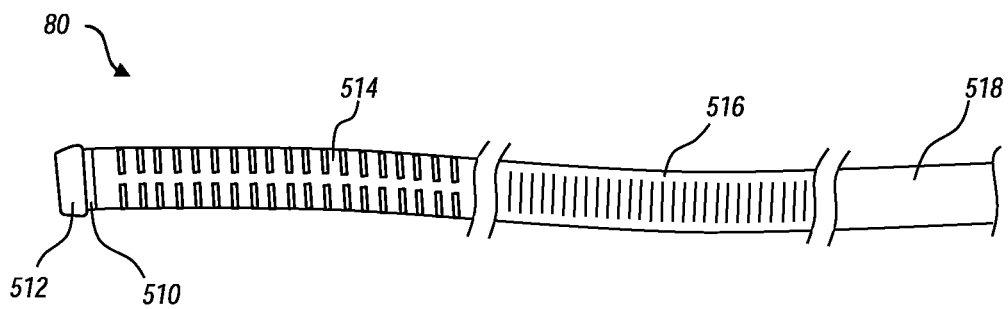
FIG. 15 illustrates the steering catheter, showing various features and sections that may be formed in the steering catheter.

FIG. 15 illustrates one embodiment of the steering catheter 80 in greater detail. In the illustrated embodiments, the steering catheter 80 includes a proximal section 518, intermediate section 516, and a distal section 514. A steering ring 510 is connected at the distal end. A distal cap 512 positioned over the steering ring 510 provide an angled/rounded surface that allows the steering catheter 80 to more effectively move and slide against the outer sheath 82 without binding. In this embodiment, the steering catheter 80 is formed as a hypotube. The proximal section 518 may remain uncut, while the intermediate section 516 and distal section 514 may be cut (e.g., laser cut) to increase flexibility. Although not shown in this view, a polymer layer surrounds the steering catheter and forms the outer layer.

In some embodiments, the steering catheter 80 is rotationally keyed to the outer sheath 82. The outer sheath 82 may include cut patterns and/or other features which are arranged to provide particular bending directions. In this embodiment, because bending of the outer sheath 82 depends upon curving of the steering catheter 80, rotational alignment of the outer sheath 82 to the steering catheter 80 is beneficial. These components may be keyed together using a key and corresponding keyway feature, slots and corresponding tabs, or other rotational keying mechanism known in the art. Alternatively, or additionally, alignment markers can be provided at the handle assembly to visually indicate alignment.

To provide effective steering and positioning at the mitral annulus, the distal section 514 is cut with a pattern which allows a bending radius of about 15 mm or less (e.g., 5 to 15 mm). The intermediate section 516 is cut to allow a bending radius of about 30 to 45 cm. The proximal section is uncut to provide the steering catheter 80 with sufficient stiffness, torquability, and pushability. The steering catheter 80 may be sized so that the inner diameter is about 0.15 to 0.20 inches, with a wall thickness of about 0.040 to 0.050 inches. As discussed above, the steering catheter 80 includes a set of tension cables which pass from the steering catheter handle to the steering ring 510. Adjusting tension of the tension cables allows the steering catheter 80 to be curved. The tension cables have a diameter that allows them to fit within the wall of the outer layer of the steering catheter 80, such as a diameter of about 0.01 to 0.02 inches, or about 0.015 to 0.018 inches.

Figure 16:
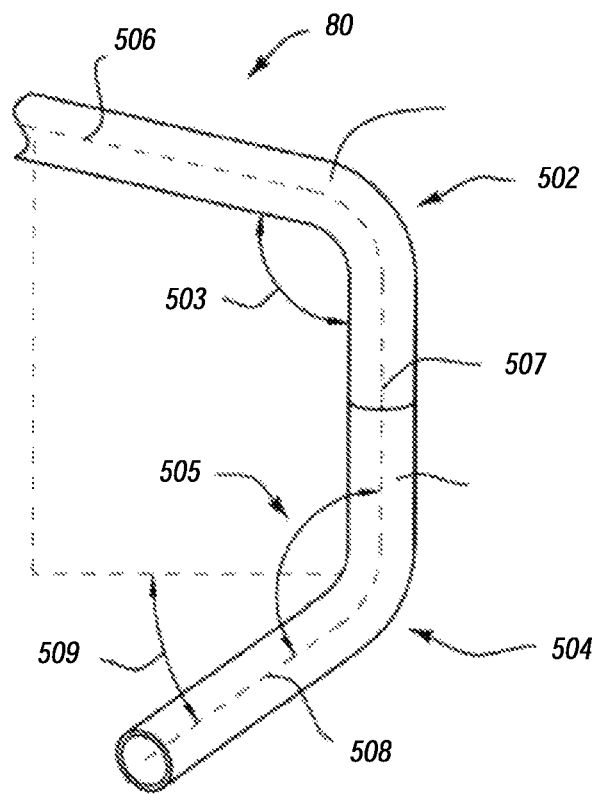
FIG. 16 illustrates the steering catheter after forming a compound curve shape to enable proper positioning of the delivery member relative to the mitral annulus.

FIG. 16 illustrates an example of a series of compound bends that the steering catheter 80 may perform during the delivery, repair, recapture, or repositioning of the intravascular device. While accessing the mitral annulus, the steering catheter 80 may be steered in at least two planes of motion. The two planes of motion may be substantially perpendicular to one another. The steering catheter 80 has a first bend 502 with a first bend angle 503 measured between a first longitudinal axis 506 and a second longitudinal axis 507. In some embodiments, the first bend angle 503 may be in a range having an upper value, a lower value, or an upper and lower value including any of 60°, 65°, 70°, 75°, 80°, 85°, 90°, 100°, 105°, 110°, 115°, 120°, 125°, 130°, 135°, 140°, 145°, 150°, 155°, 160°, 165°, 170°, or 175°. In one embodiment, the first bend angle 503 is in a range of about 90° to 120°, or is about 105°.

The steering catheter 80 has a second bend 504 having a second bend angle 505. The second bend 504 is formed between a third longitudinal axis 508 and the second longitudinal axis 507. The second bend 504 may also have a rotational angle 509 relative to a plane in which the first longitudinal axis 506 and the second longitudinal axis 507 lie. In other words, the rotational angle 509 is relative to the amount of rotation of the third longitudinal axis 508 relative to the direction of the first bend 502.

The second bend angle 505 may be in a range having an upper value, a lower value, or an upper and lower value including any of 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, or 175°, In one embodiment, the second bend angle 505 is in a range of about 80° to 110°, or is about 90°. The rotational angle 509 may be in a range having an upper value, a lower value, or an upper and lower value including any of 30°, 35°, 40°, 45°, 50°, 55°, 60°, 65°, 70°, 75°, 80°, 85°, 90°, 100°, 110°, 120°, 130°, 140°, 150°, or 160°. In one embodiment, the rotational angle 509 may be in a range of 45° to 135° or may be about 60°.

Figure 17:
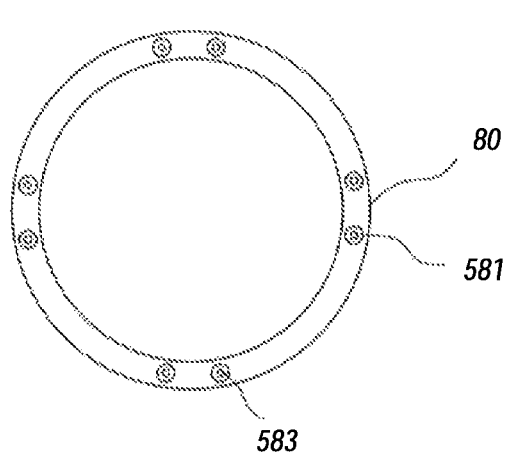
FIG. 17 illustrates a cross-sectional view of the steering catheter, showing lumens for routing tension cables through the steering catheter.

FIG. 17 is a cross-sectional view of the outer layer of the steering catheter 80, showing a series of lumen 581 for routing of the tension cables 583. In some embodiments, the lumen 581 are held open with micro-coils, at least at the distal section 514 where greater bending takes place. The micro-coils maintain effective flexibility while also keeping the lumen clear and open, while minimizing bowing, for proper operation of the tension cables 583. In some embodiments, a braid material covers the lumen 581 in the intermediate section 516 and/or proximal section 518. In one embodiment, the polymer outer layer is a polyether block amide. The polymer outer layer may be formed to be have greater flexibility at the distal section 514 than at the intermediate and proximal sections 516, 518. For example, the polymer layer at the distal section 514 may have a durometer of about 30 to 40D, or about 35D, whereas at the intermediate section 516 and/or proximal section 518 the polymer layer has a durometer of about 55 to 85D, or about 65 to 75D.

Figure 18:
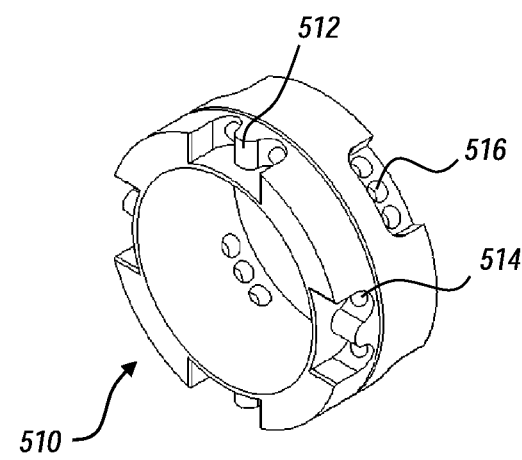
FIG. 18 illustrates a distal steering ring configured for positioning at the distal end of the steering catheter.

FIG. 18 shows the distal steering ring 510. The steering ring 510 includes a set of distal holes 514. Each pair of distal holes 514 surrounds a saddle feature 512. A tension cable may be routed distally to the steering ring 510, through one of the distal holes 514, and then over the adjacent saddle feature 512 and back through the opposite distal hole 514. The saddle feature 512 has a curved surface on which the overlying tension cable rests, which minimizes pinching of the tension cable. The steering ring 510 may also include one or more proximal holes 516, which can be used for attaching the steering ring 510 to the distal end of the steering catheter 80 (via adhesives and/or laser welding, for example).

Figure 19A:
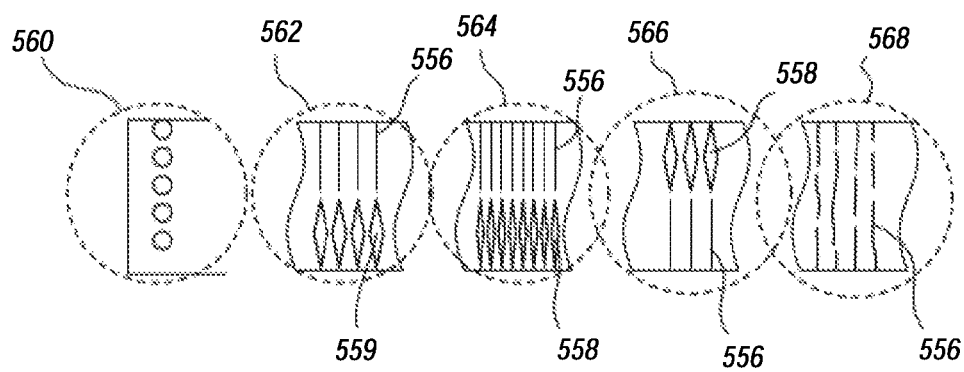
FIG. 19A illustrates various cut patterns which may be utilized in the outer sheath and/or steering catheter to provide flexibility and/or preferential bending.
Figure 19B:
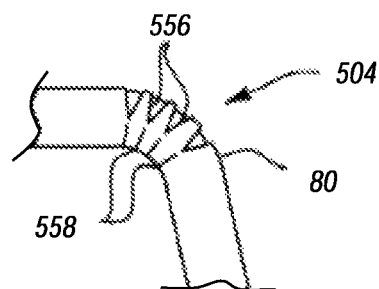
FIG. 19B illustrates bending of the steering catheter, showing features of the cut patterns which enable the bending.

FIG. 19A shows various cutting patterns that can be used in different sections of the steering catheter 80 (and corresponding sections of the outer sheath 82) to produce the desired bends. Each section can include cut patterns that can include one or more slits 556 and/or one or more island cuts 558. The slits 556 may transmit longitudinal force along the catheter and also allow expansion of the catheter when it is deflected in a direction opposite the slit 556. The island cuts 558 may allow compression of the catheter when it is deflected in a direction of the island cuts 558. For example, slits 556 and island cuts 558, when located on opposite sides from one another, may direct preferential bending of the catheter, as shown by exemplary bend 504 in FIG. 19B.

In one embodiment, illustrated in FIG. 19A, a cutting pattern can include five sections or regions 560, 562, 564, 566 and 568, with different cut patterns in each section. Such sections may be arranged as needed to provide the desired compound curve profile. For example, a first section 560 can include a plurality of holes radially spaced about the periphery of the catheter. These holes provide flexibility without forming a particular bending direction. A second section 562 provides for bending in a first direction, a third section 564 is similar to the second section 562 but with smaller sized and more closely spaced island cuts 558, a fourth section 564 provides for bending in a second direction, and a fifth section 566 includes multiple slits for adding flexibility without forming a particular bending direction. While the island cuts 558 are depicted as diamond-shaped, the island cuts 558 may have one or more other shapes, such as square, rhombohedral, triangular, rectangular, circular, oblong, other elliptical, other polygonal, irregular, or combinations thereof.

Figure 20:
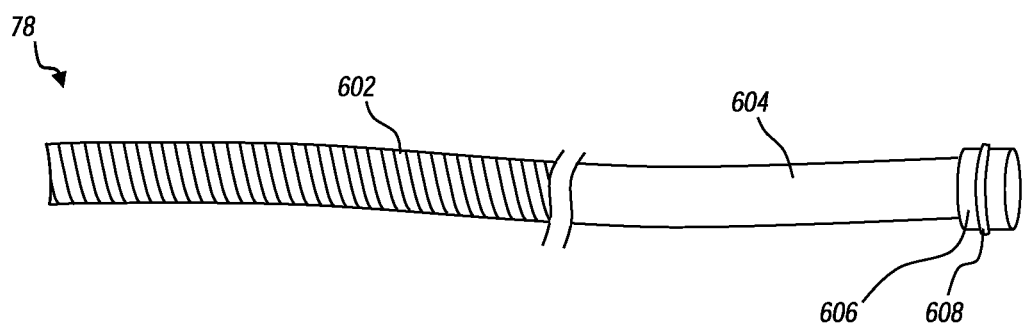
FIG. 20 illustrates a detailed view of the delivery catheter.

FIG. 20 illustrates one embodiment of the delivery catheter 78 in greater detail. The delivery catheter 78 includes a proximal section 604 and a distal section 602. At the proximal end, the delivery catheter 78 includes a seal 606 and an o-ring 608 for forming a fluid tight seal at the delivery catheter holder 136. In the illustrated embodiment, the distal section 602 is formed as a compression coil. The compression coil provides the delivery catheter 78 with ability to effectively push the intravascular device through the steering catheter 80 as part of deployment. The compression coil also provides good flexibility for advancing within the compound curve of the steering catheter 80. In this embodiment, the proximal section 604 is formed as a cut (e.g., laser cut) hypotube.

Figure 21A:
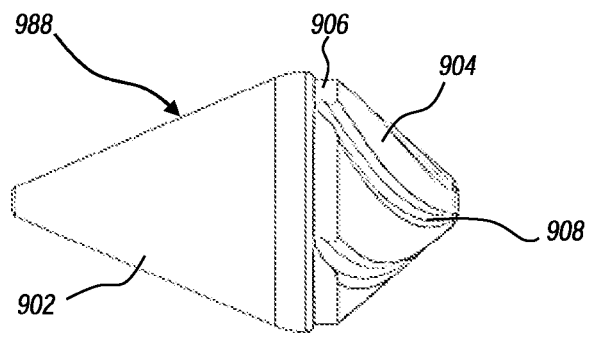
FIGS. 21A and 21B illustrate exemplary embodiments of a distal tip.

FIG. 21A illustrates one embodiment of a distal tip 988 having an active element 908 to aid in removal of the distal tip 988 in the case that it becomes caught or tangled in chordae. The illustrated embodiment includes distal portion 902, a proximal section 904, and a lip 906. The diameter of the tip at the lip 906 is sized to match an inner diameter of the distal piece so that the lip 906 can be seated within the distal piece. As shown, the active element 908 may be formed as a thread or spiraled set of grooves. The grooves preferably extend from the proximal end of the tip 988 onto the lip 906. The grooves of the active element 908 may have a pitch of about 30 to 60 degrees. The structure of such an active element allows the tip 988 to be "screwed out" of entangled chordae by rotating the guidewire tube to which the tip 988 is connected.

Figure 21B:
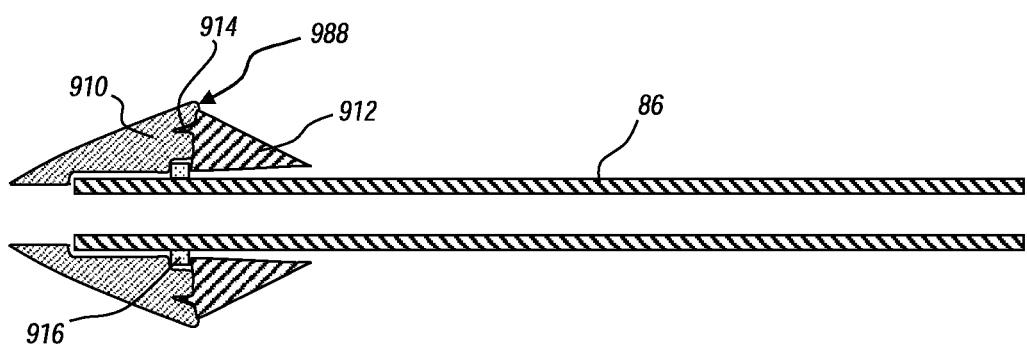

The tip 988 may be coupled to the guidewire tube 86 using an adhesive, welding, a friction fit, a threaded connection, and/or other suitable connection means. FIG. 21B illustrates, in cross-sectional view, one embodiment where the tip 988 is formed as two separate pieces. The distal piece 910 and proximal piece 912 may be fit together at a snap fit feature 914, as shown. Alternatively, the distal piece 910 and proximal piece 912 may include corresponding threads to allow a threaded connection, and/or the tip 988 may include a cutting ring fitting (e.g., metal or plastic) configured to deform to hold the separate pieces in position when the separate pieces are screwed or snapped together. The guidewire tube 86 may also include a holding ring 916 that the two-piece tip 988 can be positioned around and mechanically interfere with. The holding ring 916 may also function as a mechanical stopper. The holding ring 916 may also be formed of a radiopaque material. In some embodiments, a pouch or cavity of cyanoacrylate or other suitable adhesive is included in one of the separate pieces, and is positioned to break open to release the adhesive when the separate pieces are connected.

Exemplary Delivery Procedures

Figure 22A:
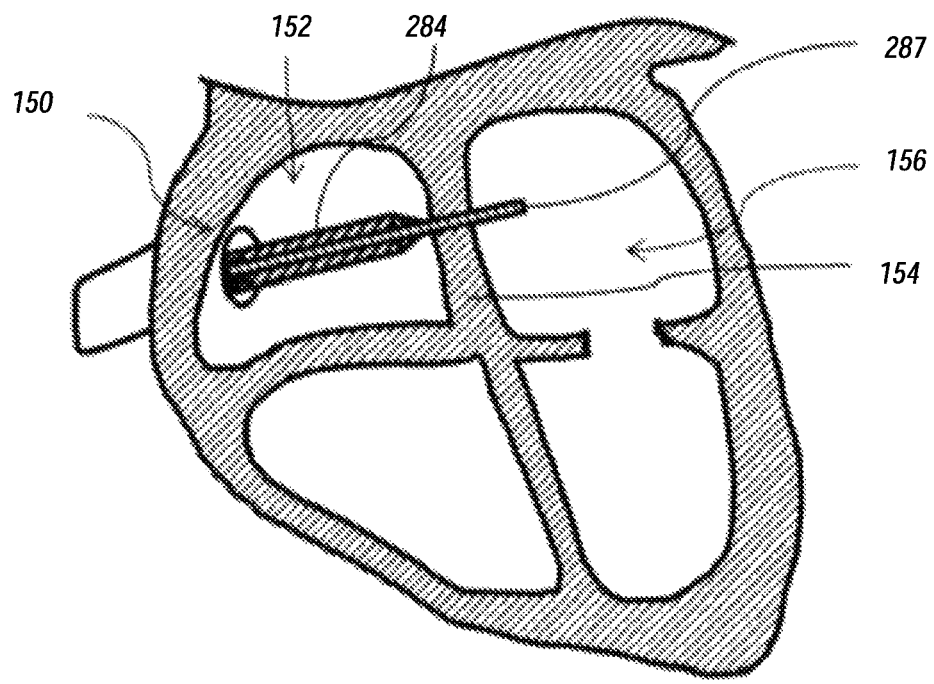
FIGS. 22A through 22E illustrate an exemplary delivery procedure for positioning the distal end of the delivery member at the mitral annulus.
Figure 22B:
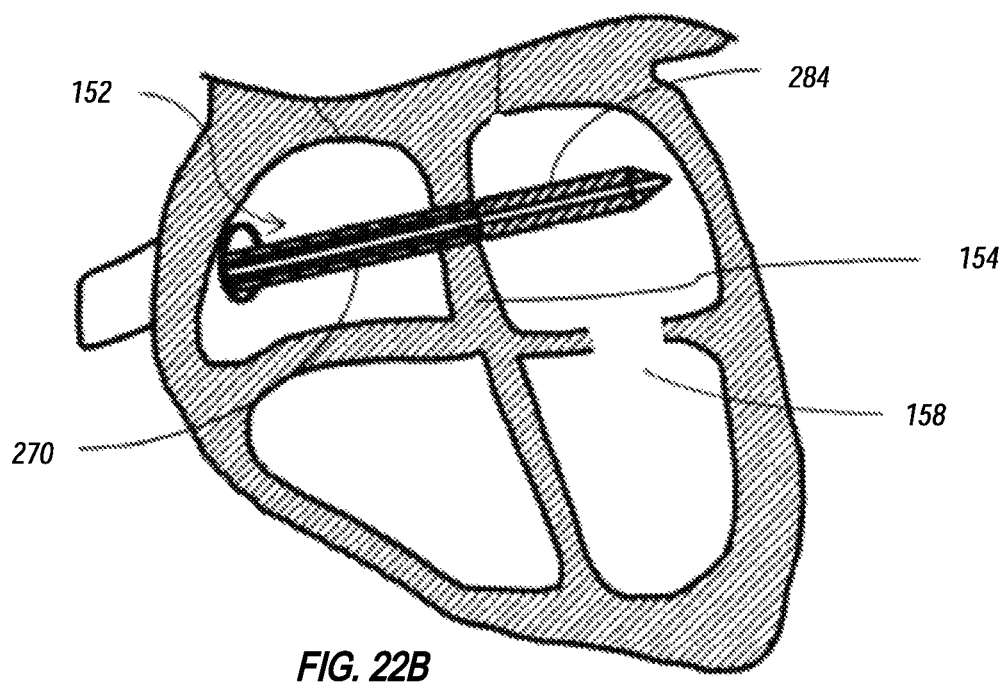

FIGS. 22A through 22E illustrate an exemplary approach for delivering the intravascular device to the mitral annulus. In some circumstances, the intravascular device, distal piece, and other associated components may be relatively rigid and/or long, which can complicate delivery. FIG. 22A illustrates an embodiment of a delivery member 270 and distal piece 284 positioned in the right atrium 152 of a heart. A guidewire 287 may be inserted through the intra-atrial septum and into the left atrium 156 of the heart. The intravascular device is then urged longitudinally through the intra-atrial septum 154 to the left atrium 156, as shown in FIG. 22B.

FIG. 22B shows the delivery member 270 and positioned in the left atrium 156. The distal piece 284 may have a longitudinal length such that the distal end of the device strikes the wall of the left atrium opposite the intra-atrial septum 154 if the distal end of the device is positioned over the mitral annulus 158 before deflecting/curving the delivery member 270.

Figure 22C:
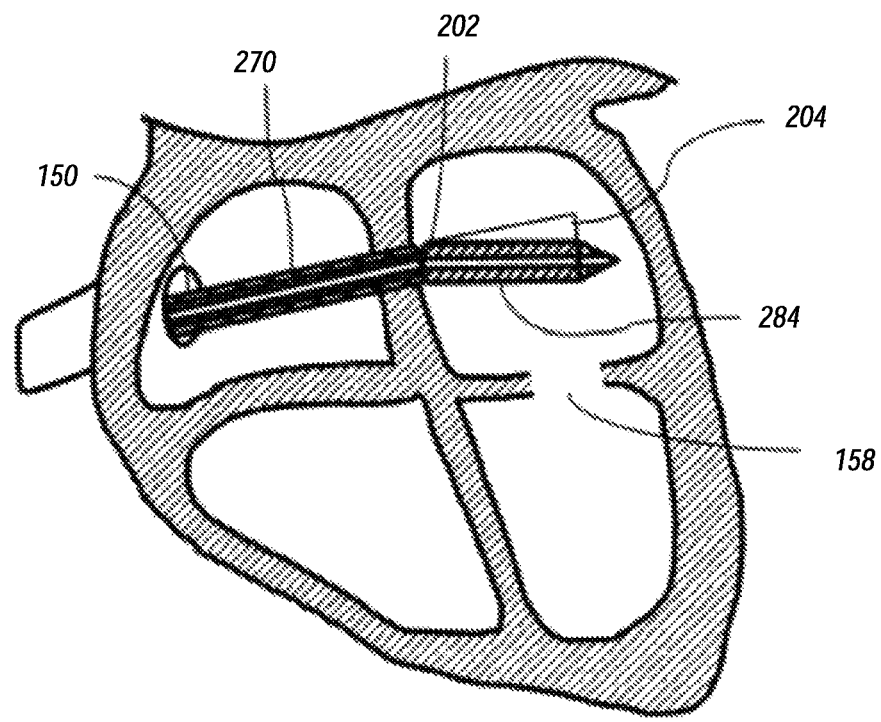

In some embodiments, the delivery member 302 is advanced until the distal tip is positioned just beyond the intra-atrial septum and just into the left atrium 156. For example, less than 5 mm, less than 4 mm, less than 3 mm, less than 2 mm, or less than 1 mm of the distal piece 284 may be located in the left atrium 156. As shown in FIG. 22C, the distal section of the device may be deflected/curved an amount toward the mitral annulus 158 by steering the steering catheter toward the target location.

Figure 22D:
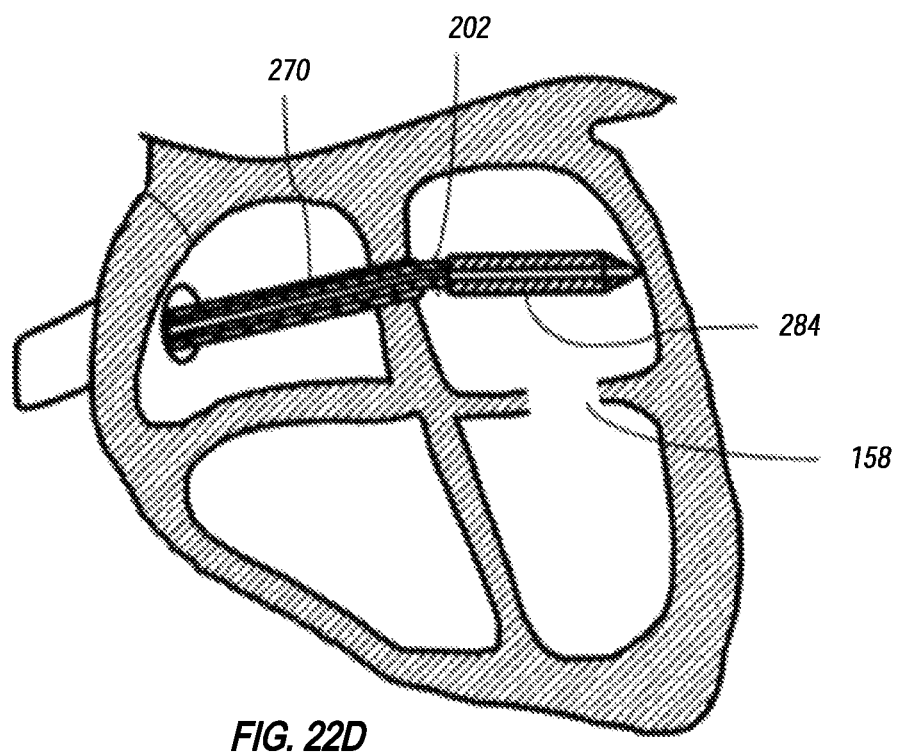
Figure 22E:
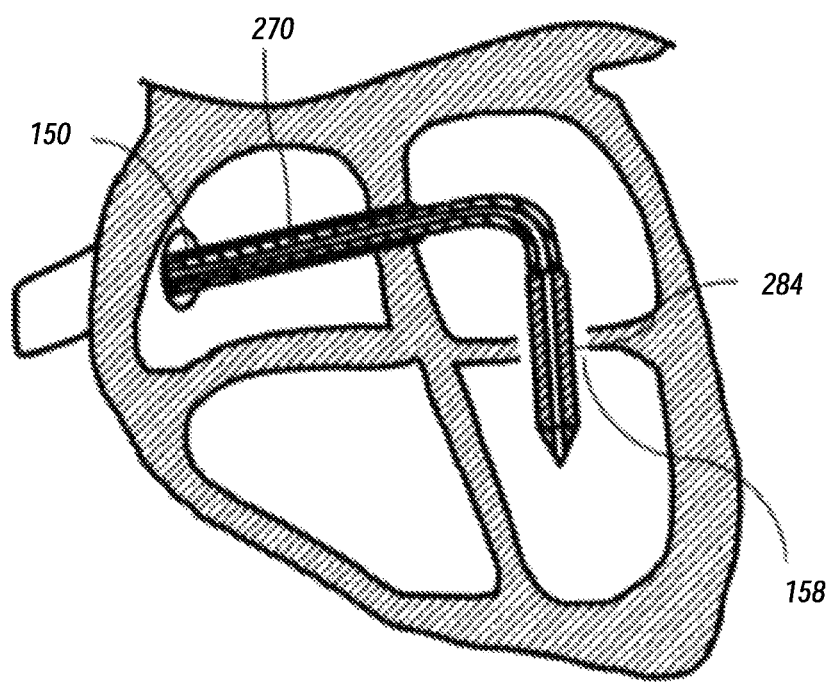

After deflecting/curving a first amount, the delivery member 270 may be longitudinally advanced further to position a greater amount of the distal piece 284 through the septum and into the left atrium, as shown in FIG. 22D. The device may be iteratively deflected/curved and advanced as necessary to achieve the desired position substantially normal to the mitral annulus as shown in FIG. 22E, while avoiding hitting against the cardiac wall.

Figure 23A:
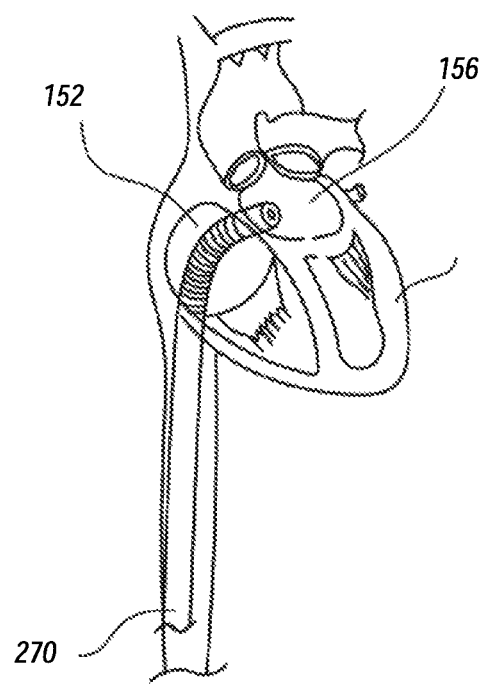
FIG. 23A depicts a path generally taken by a conventional delivery catheter through the right atrium of the heart and through the intra-atrial septum.
Figure 23B:
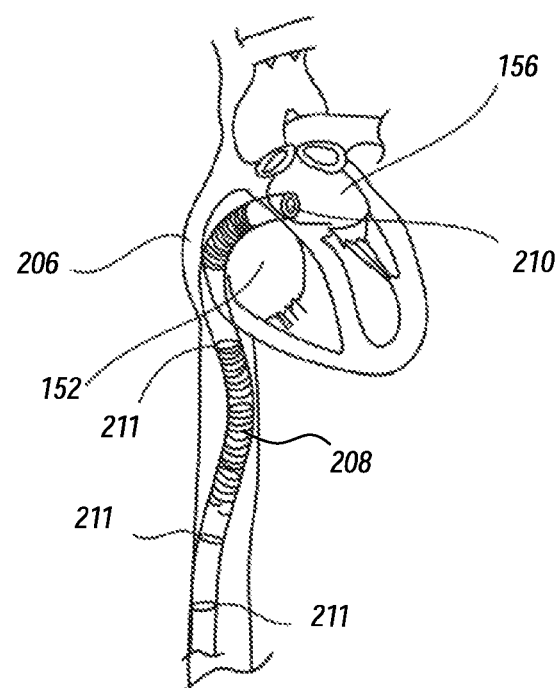
FIG. 23B depicts an improved path for the delivery member by use of various cut patterns in different sections of the delivery member.

As shown in FIGS. 23A and 23B, the right atrium 152 of a human heart provides limited space in which to bend or steer a catheter from the direction in which the inferior vena cava enters the heart to a direction in line with the intra-atrial septum. For longer interventional devices, it may be more difficult to make the necessary bend within the confines of the right atrium 152. FIG. 23A graphically depicts a path generally taken by a conventional delivery catheter through the right atrium 152 and through the intra-atrial septum to the left atrium 156.

To address this issue, the delivery member may be configured to produce a first bend at a first location 206 near a distal end 210, while also producing a second bend at a second location 208 proximal the first location 206. This can provide an improved path for the elongated delivery member, as graphically illustrated in FIG. 23B, that can provide additional space in which to allow the distal end portion of the catheter and intravascular device to make the turn within the right atrium 152. The second bend at the second location 208 can be in a direction substantially opposite to that of the first bend at the first location 206. By so doing, the second bend pushes or "kicks" the elongated delivery member in the opposite direction from the movement of the distal tip near the first location 206. This movement urges the delivery member near the first bend location 206 to move toward the wall of the right atrium 152 and creates more space for the distal tip 210 to bend and penetrate the intra-atrial septum.

Figure 24A:
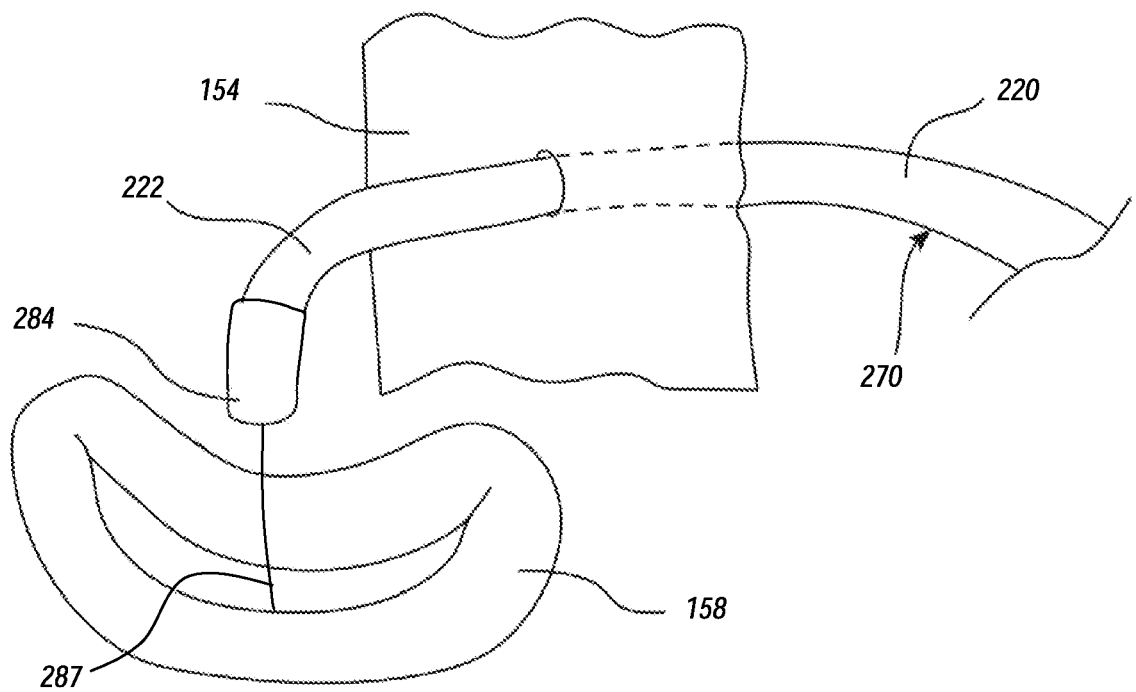
FIGS. 24A and 24B illustrate a "diving down" procedure for positioning the delivery member through the mitral valve annulus.
Figure 24B:
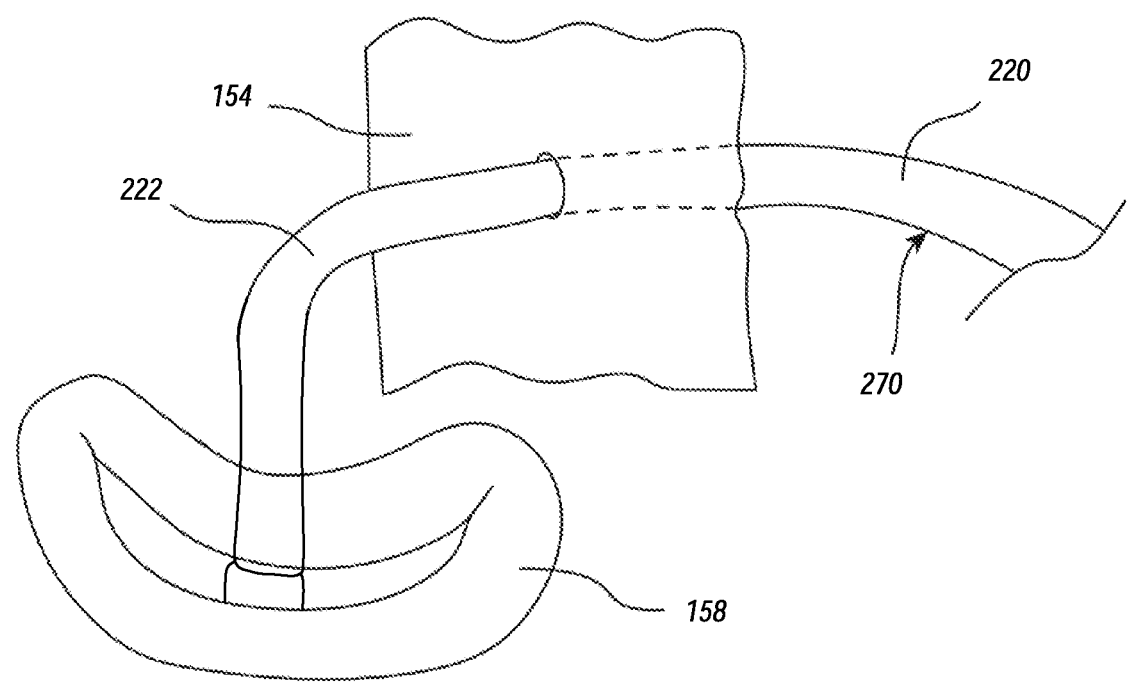

FIGS. 24A and 24B illustrate a maneuver for advancing the distal end of the delivery member 270 into the mitral annulus 158 after the distal piece 284 has been properly positioned above the mitral annulus 158 via curves/bends 220 and 222. As shown, the delivery member 270 is advanced distally forward through the mitral annulus although the compound curve shape of curves 220 and 222 is maintained. As described above with reference to FIGS. 6A and 6B, this is possible because the outer sheath, distal piece, delivery catheter, suture catheter, and guidewire tube may be advanced relative to the steering catheter while the steering catheter maintains its compound curve shape.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that deviate by less than or equal to 5%, 1%, 0.1%, or 0.01% of a stated value.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

The invention claimed is:

1. A delivery system for delivering an implantable intravascular device to a targeted cardiac valve, the delivery system comprising:
    a handle assembly;
    an elongated delivery member coupled to the handle assembly and extending distally from the handle assembly, the elongated delivery member being configured to detachably couple to an intravascular device, the elongated delivery member comprising:
        an outer sheath having a distal piece proximal to an atraumatic distal tip of the elongated delivery member, the distal piece being configured to house the intravascular device in a pre-deployed configuration, the atraumatic distal tip remaining distal the distal piece during deployment of the intravascular device from the distal piece;
        a guidewire tube extending through the delivery member and through the distal piece to attach to the distal tip, the distal tip being configured to connect to or seat against a distal side of the distal piece, the guidewire tube being configured to receive a guidewire, the guidewire tube and the distal tip being translatable in relation to the distal piece;
        a steering catheter configured to curve the delivery member in a compound curve that enables intravascular delivery of the delivery member to the targeted cardiac valve;
        a delivery catheter disposed within the steering catheter and configured to longitudinally translate the intravascular device relative to the outer sheath; and
        a suture catheter disposed within the delivery catheter and having one or more tethers configured to detachably couple to the intravascular device, the suture catheter being longitudinally translatable relative to the delivery catheter to enable adjustment of tension in the one or more tethers.

2. The delivery system of claim 1, wherein the steering catheter includes a plurality of tension cables and corresponding tension cable lumens, the tension cables providing for steering of the steering catheter by adjusting tension in the tension cables.

3. The delivery system of claim 2, wherein each tension cable lumen includes a micro coil along at least a distal section of the steering catheter.

4. The delivery system of claim 1, wherein the steering catheter is formed as a hypotube, the hypotube having a cut pattern that increases the flexibility of the hypotube relative to an uncut section of hypotube.

5. The delivery system of claim 4, wherein the hypotube includes a distal section, an intermediate section, and a proximal section, the distal section having a cut pattern which enables a bend radius of about 5 to 15 mm, and wherein the intermediate section has a cut pattern which provides a larger bend radius than of the distal section.

6. The delivery system of claim 1, wherein the distal piece includes a plurality of microfabricated cuts along at least a proximal section of the distal piece, the microfabricated cuts being configured to provide bending in a single plane.

7. The delivery system of claim 1, wherein the outer sheath includes a coil and a braided sleeve.

8. The delivery system of claim 7, wherein the coil is formed from a coil wire having a "D" shaped cross section.

9. The delivery system of claim 7, wherein the outer sheath further includes a fluid impermeable flexible polymer cover disposed over the coil and braided sleeve.

10. The delivery system of claim 1, wherein the distal piece is rotationally decoupled from the remainder of the outer sheath.

11. The delivery system of claim 1, wherein the outer sheath is coupled to the handle assembly with a swivel connection that enables the outer sheath to rotationally swivel relative to the handle assembly.

12. The delivery system of claim 1, wherein the delivery catheter includes a compression coil at least at a distal section.

13. The delivery system of claim 1, wherein the handle assembly is supported by a fixture, the fixture including a plurality of supports which support the outer sheath, a steering catheter handle, a delivery catheter holder, and a suture catheter holder, the fixture including adjustable controls which enable movement of components of the delivery member relative to other components of the delivery member.

14. The delivery system of claim 13, wherein the fixture includes a delivery device adjustor for longitudinally translating the entire delivery device relative to a base.

15. The delivery system of claim 13, wherein the fixture includes an outer sheath adjustor for translating the outer sheath relative to other components of the delivery member.

16. The delivery system of claim 13, wherein the fixture includes a deployment adjustor for translating the delivery catheter, outer sheath, and suture catheter relative to the steering catheter.

17. The delivery system of claim 1, wherein the handle assembly includes a delivery catheter holder, a suture catheter holder, and a suture catheter adjustor, the suture catheter adjustor being coupled to the delivery catheter holder, and the suture catheter holder including threads which engage with corresponding threads of the suture catheter adjustor such that rotation of the suture catheter adjustor translates the suture catheter holder relative to the delivery catheter holder.

18. A delivery system for intravascularly delivering an implantable intravascular device to the mitral annulus, the delivery system comprising:

an elongated delivery member coupled to a handle assembly and extending distally from the handle assembly, the delivery member having an atraumatic distal end and being configured to detachably receive an intravascular device proximal the atraumatic distal end, the delivery member comprising:

an outer sheath having a distal piece proximal a distal tip forming the atraumatic distal end of the elongated delivery member, the distal piece being configured to house and constrain the intravascular device, with the distal tip closing an end of the distal piece, in a pre-deployed configuration, the atraumatic distal tip remaining distal the distal piece during deployment of the intravascular device from the distal piece;

a steering catheter configured to curve the delivery member in a compound curve that enables intravascular delivery of the delivery member to the targeted cardiac valve;

a delivery catheter disposed within the steering catheter and configured to longitudinally translate the intravascular device relative to the outer sheath;

a suture catheter disposed within the delivery catheter and having one or more tethers configured to detachably couple to a proximal section of the intravascular device, the suture catheter being longitudinally translatable relative to the delivery catheter to enable adjustment of tension in the one or more tethers; and a guidewire tube extending through the delivery member and through the distal piece to attach to the distal tip, the distal tip being configured to connect to or seat against a distal side of the distal piece, the guidewire tube being configured to receive a guidewire, the guidewire tube and the distal tip being translatable in relation to the distal piece; and a handle assembly, the handle assembly comprising:

an outer sheath holder coupled to the outer sheath at the proximal end of the outer sheath;

a steering catheter handle disposed proximal of the outer sheath holder, a proximal end of the steering catheter being coupled to the steering catheter handle and the steering catheter extending distally therefrom into the outer sheath;

a delivery catheter handle disposed proximal of the steering catheter handle, a proximal end of the delivery catheter being coupled to the delivery catheter handle and the delivery catheter extending distally therefrom into the steering catheter; and a suture catheter handle disposed proximal of the delivery catheter handle, a proximal end of the suture catheter being coupled to the delivery suture catheter handle and extending distally therefrom into the delivery catheter.

19. A delivery system for intravascularly delivering an implantable intravascular device to the mitral annulus, the delivery system comprising:

an elongated delivery member coupled to a handle assembly and extending distally from the handle assembly, the elongate delivery member being configured to detachably couple to an intravascular device received at the distal end, the delivery member comprising:

an outer sheath having a distal piece forming, with an atraumatic distal tip, the distal end of the elongated delivery member, the distal piece being configured to hold the intravascular device in a pre-deployed configuration with the atraumatic distal tip closing an end of the distal piece to form an enclosed space that constrains the implantable intravascular device during delivery of the implantable intravascular device to the mitral annulus, the atraumatic distal tip remaining distal the distal piece during deployment of the intravascular device from the distal piece;

a steering catheter configured to curve the delivery member in a compound curve that enables intravascular delivery of the delivery member to the targeted cardiac valve;

a delivery catheter disposed within the steering catheter and configured to longitudinally translate the intravascular device relative to the outer sheath;

a suture catheter disposed within the delivery catheter and having one or more tethers configured to detachably couple to the intravascular device, the suture catheter being longitudinally translatable relative to the delivery catheter to enable adjustment of tension in the one or more tethers; and a guidewire tube extending through the delivery member and through the distal piece to attach to the distal tip, the distal tip being configured to connect to or seat against a distal side of the distal piece, the guidewire tube being configured to receive a guidewire, the guidewire tube and the distal tip being translatable in relation to the distal piece; and a handle assembly, the handle assembly including an outer sheath holder, a steering catheter handle, a delivery catheter holder, and a suture catheter holder; and a fixture configured to support the handle assembly, the fixture including:

a delivery device adjustor for longitudinally translating the entire delivery device relative to a base;

an outer sheath adjustor for translating the outer sheath relative to other components of the delivery member; and a deployment adjustor for translating the delivery catheter, outer sheath, and suture catheter relative to the steering catheter.

* * * * *